(12) United States Patent
Belkin et al.

(10) Patent No.: US 10,765,799 B2
(45) Date of Patent: Sep. 8, 2020

(54) FAIL-SAFE DRUG INFUSION THERAPY SYSTEM

(71) Applicant: ICU Medical, Inc., San Clemente, CA (US)

(72) Inventors: Anatoly S. Belkin, Glenview, IL (US); William K. Day, Hoffman Estates, IL (US); Steve J. Lindo, Chicago, IL (US); James P. Roman, Nashotah, WI (US); Andrei T. Stratan, Mountain View, CA (US)

(73) Assignee: ICU Medical, Inc., San Clemente, CA (US)

( * ) Notice: Subject to any disclaimer, the term of this patent is extended or adjusted under 35 U.S.C. 154(b) by 323 days.

(21) Appl. No.: 15/604,007

(22) Filed: May 24, 2017

(65) Prior Publication Data
US 2017/0319780 A1 Nov. 9, 2017

Related U.S. Application Data

(63) Continuation of application No. 14/490,450, filed on Sep. 18, 2014, now Pat. No. 9,662,436.
(Continued)

(51) Int. Cl.
*A61M 5/14* (2006.01)
*A61M 5/142* (2006.01)
*G06F 19/00* (2018.01)

(52) U.S. Cl.
CPC ......... *A61M 5/142* (2013.01); *G06F 19/3418* (2013.01); *G06F 19/3468* (2013.01);
(Continued)

(58) Field of Classification Search
CPC ........ A61M 5/142; A61M 2005/14208; A61M 2205/17; A61M 2205/35; A61M 2205/50;
(Continued)

(56) References Cited

U.S. PATENT DOCUMENTS 4,024,864 A  5/1977  Davies et al.
4,055,175 A  10/1977 Clemens et al.
(Continued)

FOREIGN PATENT DOCUMENTS

CA  2 060 151  8/1997
CA  2 125 300  10/1999
(Continued)

OTHER PUBLICATIONS

Cardinal Health, "Alaris® Syringe Pumps" Technical Service Manual, Copyright 2002-2006, Issue 9, pp. 1-88, http://www.frankshospitalworkshop.com/equipment/documents/infusion_pumps/service_manuals/Cardinal_Alaris_-_Service_Manual.pdf.
(Continued)

*Primary Examiner* — Amber R Stiles
(74) *Attorney, Agent, or Firm* — Knobbe Martens Olson & Bear, LLP

(57) ABSTRACT

A fail-safe drug infusion system, including a user interface controller (UIC) and at least one pump motor controller (PMC), with protocols that enable the PMC to operate therapy delivery for a limited amount of time if the UIC fails or the communication link between the UIC and the PMC is interrupted. Includes synchronization methods to synchronize the delivery information back to the UIC after the UIC reboots or after the communication link is restored. The PMC may apply intelligent fail-safe drug infusion therapy by temporarily displaying therapy information, for example information normally displayed by the UIC, while taking control of alarm signaling and providing minimal user control of the therapy until the UIC restores itself, the infusion completes normally, or the user stops the infusion. If the PMC becomes inoperable, the UIC may wait for the PMC to reboot, or attempt to switch infusion channels to provide robust drug infusion.

16 Claims, 6 Drawing Sheets

Related U.S. Application Data

(60) Provisional application No. 61/880,656, filed on Sep. 20, 2013.

(52) U.S. Cl.
CPC ............ *A61M 2005/14208* (2013.01); *A61M 2205/17* (2013.01); *A61M 2205/35* (2013.01); *A61M 2205/50* (2013.01); *A61M 2205/502* (2013.01); *A61M 2205/52* (2013.01)

(58) Field of Classification Search
CPC ......... A61M 2205/52; A61M 2205/502; G06F 19/3468; G06F 19/3418
See application file for complete search history.

(56) References Cited

U.S. PATENT DOCUMENTS

| | | |
|---|---|---|
| 4,151,845 A | 5/1979 | Clemens |
| 4,213,454 A | 7/1980 | Shim |
| 4,240,438 A | 12/1980 | Updike et al. |
| 4,280,494 A | 7/1981 | Cosgrove et al. |
| 4,308,866 A | 1/1982 | Jeliffe |
| 4,370,983 A | 2/1983 | Lichtenstein et al. |
| 4,373,527 A | 2/1983 | Fischell |
| 4,392,849 A | 7/1983 | Petre et al. |
| 4,395,259 A | 7/1983 | Prestele et al. |
| 4,457,751 A | 7/1984 | Rodler |
| 4,464,170 A | 8/1984 | Clemens |
| 4,469,481 A | 9/1984 | Kobayashi |
| 4,475,901 A | 10/1984 | Kraegen et al. |
| 4,494,950 A | 1/1985 | Fischell |
| 4,498,843 A | 2/1985 | Schneider et al. |
| 4,515,584 A | 5/1985 | Abe et al. |
| 4,526,568 A | 7/1985 | Clemens et al. |
| 4,529,401 A | 7/1985 | Leslie et al. |
| 4,543,955 A | 10/1985 | Schroeppel |
| 4,551,133 A | 11/1985 | Zegers de Beyl et al. |
| 4,553,958 A | 11/1985 | LeCocq |
| 4,559,037 A | 12/1985 | Franetzki et al. |
| 4,613,937 A | 9/1986 | Batty |
| 4,624,661 A | 11/1986 | Arimond |
| 4,633,878 A | 1/1987 | Bombardieri |
| 4,634,426 A | 1/1987 | Kamen |
| 4,634,427 A | 1/1987 | Hannula et al. |
| 4,674,652 A | 6/1987 | Aten et al. |
| 4,676,776 A | 6/1987 | Howson et al. |
| 4,679,562 A | 7/1987 | Luksha |
| 4,685,903 A | 8/1987 | Cable et al. |
| 4,695,954 A | 9/1987 | Rose |
| 4,696,671 A | 9/1987 | Epstein et al. |
| 4,714,462 A | 12/1987 | DiDomenico |
| 4,722,734 A | 2/1988 | Kolin |
| 4,731,051 A | 3/1988 | Fischell |
| 4,741,732 A | 5/1988 | Crankshaw et al. |
| 4,756,706 A | 7/1988 | Kerns et al. |
| 4,776,842 A | 10/1988 | Franetzki et al. |
| 4,785,969 A | 11/1988 | McLaughlin |
| 4,803,625 A | 2/1989 | Fu et al. |
| 4,835,372 A | 5/1989 | Gombrich et al. |
| 4,838,275 A | 6/1989 | Lee |
| 4,838,856 A | 6/1989 | Mulreany et al. |
| 4,838,857 A | 6/1989 | Strowe et al. |
| 4,854,324 A | 8/1989 | Hirschman et al. |
| 4,857,716 A | 8/1989 | Gombrich et al. |
| 4,858,154 A | 8/1989 | Anderson et al. |
| 4,898,578 A | 2/1990 | Rubalcaba, Jr. |
| 4,908,017 A | 3/1990 | Howson et al. |
| 4,933,873 A | 6/1990 | Kaufman et al. |
| 4,943,279 A | 7/1990 | Samiotes et al. |
| 4,946,439 A | 8/1990 | Eggers |
| 4,953,745 A | 9/1990 | Rowlett |
| 4,978,335 A | 12/1990 | Arthur, III |
| 5,000,739 A | 3/1991 | Kulisz et al. |
| 5,010,473 A | 4/1991 | Jacobs |
| 5,014,698 A | 5/1991 | Cohen |
| 5,016,172 A | 5/1991 | Dessertine |
| 5,026,084 A | 6/1991 | Paisfield |
| 5,034,004 A | 7/1991 | Crankshaw |
| 5,041,086 A | 8/1991 | Koenig et al. |
| 5,058,161 A | 10/1991 | Weiss |
| 5,078,683 A | 1/1992 | Sancoff et al. |
| 5,084,828 A | 1/1992 | Kaufman et al. |
| 5,088,981 A | 2/1992 | Howson et al. |
| 5,097,505 A | 3/1992 | Weiss |
| 5,100,380 A | 3/1992 | Epstein et al. |
| 5,102,392 A | 4/1992 | Sakai et al. |
| 5,104,374 A | 4/1992 | Bishko et al. |
| 5,109,850 A | 5/1992 | Blanco et al. |
| 5,131,816 A | 7/1992 | Brown |
| 5,142,484 A | 8/1992 | Kaufman et al. |
| 5,153,827 A | 10/1992 | Coutre et al. |
| 5,157,640 A | 10/1992 | Backner |
| 5,161,222 A | 11/1992 | Montejo et al. |
| 5,177,993 A | 1/1993 | Beckman et al. |
| 5,181,910 A | 1/1993 | Scanlon |
| 5,190,522 A | 3/1993 | Wocicki et al. |
| 5,199,439 A | 4/1993 | Zimmerman et al. |
| 5,200,891 A | 4/1993 | Kehr et al. |
| 5,216,597 A | 6/1993 | Beckers |
| 5,221,268 A | 6/1993 | Barton et al. |
| 5,230,061 A | 7/1993 | Welch |
| 5,243,982 A | 9/1993 | Möstl et al. |
| 5,244,463 A | 9/1993 | Cordner, Jr. et al. |
| 5,249,260 A | 9/1993 | Nigawara et al. |
| 5,256,156 A | 10/1993 | Kern et al. |
| 5,256,157 A | 10/1993 | Samiotes et al. |
| 5,261,702 A | 11/1993 | Mayfield |
| 5,317,506 A | 5/1994 | Coutre et al. |
| 5,319,355 A | 6/1994 | Russek |
| 5,319,363 A | 6/1994 | Welch et al. |
| 5,330,634 A | 7/1994 | Wong et al. |
| 5,338,157 A | 8/1994 | Blomquist |
| 5,341,476 A | 8/1994 | Lowell |
| 5,364,346 A | 11/1994 | Schrezenmeir |
| 5,366,346 A | 11/1994 | Danby |
| 5,368,562 A | 11/1994 | Blomquist et al. |
| 5,373,454 A | 12/1994 | Kanda et al. |
| 5,376,070 A | 12/1994 | Purvis et al. |
| 5,378,231 A | 1/1995 | Johnson et al. |
| 5,389,071 A | 2/1995 | Kawahara et al. |
| 5,389,078 A | 2/1995 | Zalesky et al. |
| 5,417,222 A | 5/1995 | Dempsey et al. |
| 5,423,748 A | 6/1995 | Uhala |
| 5,429,602 A | 7/1995 | Hauser |
| 5,431,627 A | 7/1995 | Pastrone et al. |
| 5,432,777 A | 7/1995 | Le Boudec et al. |
| 5,445,621 A | 8/1995 | Poli et al. |
| 5,447,164 A | 9/1995 | Shaya et al. |
| 5,455,851 A | 10/1995 | Chaco et al. |
| 5,461,365 A | 10/1995 | Schlager et al. |
| 5,464,392 A | 11/1995 | Epstein et al. |
| 5,465,082 A | 11/1995 | Chaco |
| 5,485,408 A | 1/1996 | Blomquist |
| 5,486,286 A | 1/1996 | Peterson et al. |
| 5,493,430 A | 2/1996 | Lu et al. |
| 5,496,273 A | 3/1996 | Pastrone et al. |
| 5,505,828 A | 4/1996 | Wong et al. |
| 5,507,288 A | 4/1996 | Bocker et al. |
| 5,507,786 A | 4/1996 | Morgan et al. |
| 5,508,499 A | 4/1996 | Ferrario |
| 5,515,713 A | 5/1996 | Saugues et al. |
| 5,520,637 A | 5/1996 | Pager et al. |
| 5,522,798 A | 6/1996 | Johnson et al. |
| 5,547,470 A | 8/1996 | Johnson et al. |
| 5,554,013 A | 9/1996 | Owens et al. |
| 5,562,615 A | 10/1996 | Nassif |
| 5,577,169 A | 11/1996 | Prezioso |
| 5,582,323 A | 12/1996 | Kurtenbach |
| 5,582,593 A | 12/1996 | Hultman |
| 5,594,786 A | 1/1997 | Chaco et al. |
| 5,598,519 A | 1/1997 | Narayanan |
| 5,620,608 A | 4/1997 | Rosa et al. |
| 5,630,710 A | 5/1997 | Tune et al. |

(56) References Cited

U.S. PATENT DOCUMENTS

| | | |
|---|---|---|
| 5,636,044 A | 6/1997 | Yuan et al. |
| 5,643,212 A | 7/1997 | Coutre et al. |
| 5,651,775 A | 7/1997 | Walker et al. |
| 5,658,131 A | 8/1997 | Aoki et al. |
| 5,658,250 A | 8/1997 | Blomquist et al. |
| 5,665,065 A | 9/1997 | Colman et al. |
| 5,669,877 A | 9/1997 | Blomquist |
| 5,672,154 A | 9/1997 | Sillén et al. |
| 5,681,285 A | 10/1997 | Ford et al. |
| 5,685,844 A | 11/1997 | Marttila |
| 5,687,717 A | 11/1997 | Halpern et al. |
| 5,689,229 A | 11/1997 | Chaco et al. |
| 5,697,899 A | 12/1997 | Hillman et al. |
| 5,699,509 A | 12/1997 | Gary et al. |
| 5,713,856 A | 2/1998 | Eggers et al. |
| 5,718,562 A | 2/1998 | Lawless et al. |
| 5,719,761 A | 2/1998 | Gatti et al. |
| 5,733,259 A | 3/1998 | Valcke et al. |
| 5,738,102 A | 4/1998 | Lemelson |
| 5,744,027 A | 4/1998 | Connell et al. |
| 5,752,621 A | 5/1998 | Passamante |
| 5,754,111 A | 5/1998 | Garcia |
| 5,764,034 A | 6/1998 | Bowman et al. |
| 5,764,159 A | 6/1998 | Neftel et al. |
| 5,772,635 A | 6/1998 | Dastur et al. |
| 5,774,865 A | 6/1998 | Glynn |
| 5,778,256 A | 7/1998 | Darbee |
| 5,778,345 A | 7/1998 | McCartney |
| 5,781,442 A | 7/1998 | Engleson et al. |
| 5,782,805 A | 7/1998 | Meinzer et al. |
| 5,788,669 A | 8/1998 | Peterson |
| 5,797,515 A | 8/1998 | Liff et al. |
| 5,800,387 A | 9/1998 | Duffy et al. |
| 5,814,015 A | 9/1998 | Gargano et al. |
| 5,822,544 A | 10/1998 | Chaco et al. |
| 5,822,715 A | 10/1998 | Worthington et al. |
| 5,827,179 A | 10/1998 | Lichter et al. |
| 5,832,448 A | 11/1998 | Brown |
| 5,836,910 A | 11/1998 | Duffy et al. |
| 5,850,344 A | 12/1998 | Conkright |
| 5,867,821 A | 2/1999 | Ballantyne et al. |
| 5,870,733 A | 2/1999 | Bass et al. |
| 5,871,465 A | 2/1999 | Vasko |
| 5,873,731 A | 2/1999 | Predergast |
| 5,885,245 A | 3/1999 | Lynch et al. |
| 5,897,493 A | 4/1999 | Brown |
| 5,897,498 A | 4/1999 | Canfield, II et al. |
| 5,910,252 A | 6/1999 | Truitt et al. |
| 5,912,818 A | 6/1999 | McGrady et al. |
| 5,915,240 A | 6/1999 | Karpf |
| 5,920,054 A | 7/1999 | Uber, III |
| 5,920,263 A | 7/1999 | Huttenhoff et al. |
| 5,924,074 A | 7/1999 | Evans |
| 5,931,764 A | 8/1999 | Freeman et al. |
| 5,935,099 A | 8/1999 | Peterson et al. |
| 5,935,106 A | 8/1999 | Olsen |
| 5,941,846 A | 8/1999 | Duffy et al. |
| 5,956,501 A | 9/1999 | Brown |
| 5,957,885 A | 9/1999 | Bollish et al. |
| 5,960,085 A | 9/1999 | de la Huerga |
| 5,961,448 A | 10/1999 | Swenson et al. |
| 5,967,559 A | 10/1999 | Abramowitz |
| 5,971,594 A | 10/1999 | Sahai et al. |
| 5,975,081 A | 11/1999 | Hood et al. |
| 5,990,838 A | 11/1999 | Burns et al. |
| 5,997,476 A | 12/1999 | Brown |
| 6,000,828 A | 12/1999 | Leet |
| 6,003,006 A | 12/1999 | Colella et al. |
| 6,012,034 A | 1/2000 | Hamparian et al. |
| 6,017,318 A | 1/2000 | Gauthier et al. |
| 6,021,392 A | 2/2000 | Lester et al. |
| 6,024,539 A | 2/2000 | Blomquist |
| 6,032,155 A | 2/2000 | de la Huerga |
| 6,032,676 A | 3/2000 | Moore |
| 6,073,106 A | 6/2000 | Rozen et al. |
| 6,104,295 A | 8/2000 | Gaisser et al. |
| 6,112,182 A | 8/2000 | Akers et al. |
| RE36,871 E | 9/2000 | Epstein et al. |
| 6,115,390 A | 9/2000 | Chuah |
| 6,122,536 A | 9/2000 | Sun et al. |
| 6,126,637 A | 10/2000 | Kriesel et al. |
| 6,135,949 A | 10/2000 | Russo et al. |
| 6,150,942 A | 11/2000 | O'Brien |
| 6,151,643 A | 11/2000 | Cheng et al. |
| 6,157,914 A | 12/2000 | Seto et al. |
| 6,159,147 A | 12/2000 | Lichter et al. |
| 6,167,567 A | 12/2000 | Chiles et al. |
| 6,182,667 B1 | 2/2001 | Hanks et al. |
| 6,189,105 B1 | 2/2001 | Lopes |
| 6,195,589 B1 | 2/2001 | Ketcham |
| 6,208,974 B1 | 3/2001 | Campbell et al. |
| 6,222,323 B1 | 4/2001 | Yamashita et al. |
| 6,223,440 B1 | 5/2001 | Rashman |
| 6,226,277 B1 | 5/2001 | Chuah |
| 6,227,371 B1 | 5/2001 | Song |
| 6,234,176 B1 | 5/2001 | Domae et al. |
| 6,241,704 B1 | 6/2001 | Peterson et al. |
| 6,248,067 B1 | 6/2001 | Causey, III et al. |
| 6,249,705 B1 | 6/2001 | Snell |
| 6,257,265 B1 | 7/2001 | Brunner et al. |
| 6,259,355 B1 | 7/2001 | Chaco et al. |
| 6,269,340 B1 | 7/2001 | Ford et al. |
| 6,270,455 B1 | 8/2001 | Brown |
| 6,271,813 B1 | 8/2001 | Palalau |
| 6,277,072 B1 | 8/2001 | Bardy |
| 6,280,380 B1 | 8/2001 | Bardy |
| 6,283,761 B1 | 9/2001 | Joao |
| 6,285,665 B1 | 9/2001 | Chuah |
| 6,292,860 B1 | 9/2001 | Cochcroft, Jr. |
| 6,312,378 B1 | 11/2001 | Bardy |
| 6,327,254 B1 | 12/2001 | Chuah |
| 6,330,008 B1 | 12/2001 | Razdow et al. |
| 6,339,718 B1 | 1/2002 | Zatezalo et al. |
| 6,346,886 B1 | 2/2002 | de la Huerga |
| 6,363,282 B1 | 3/2002 | Nichols et al. |
| 6,371,719 B1 | 4/2002 | Hildebrandt |
| 6,377,548 B1 | 4/2002 | Chuah |
| 6,388,951 B1 | 5/2002 | Matsumoto et al. |
| 6,406,426 B1 | 6/2002 | Reuss et al. |
| 6,408,330 B1 | 6/2002 | de la Huerga |
| 6,418,334 B1 | 7/2002 | Unger et al. |
| 6,427,088 B1 | 7/2002 | Bowman et al. |
| 6,428,483 B1 | 8/2002 | Carlebach |
| 6,442,432 B2 | 8/2002 | Lee |
| 6,469,991 B1 | 10/2002 | Chuah |
| 6,475,180 B2 | 11/2002 | Peterson et al. |
| 6,482,158 B2 | 11/2002 | Mault |
| 6,485,418 B2 | 11/2002 | Yasushi et al. |
| 6,494,694 B2 | 12/2002 | Lawless et al. |
| 6,494,831 B1 | 12/2002 | Koritzinsky |
| 6,497,680 B1 | 12/2002 | Holst et al. |
| 6,514,460 B1 | 2/2003 | Fendrock |
| 6,517,482 B1 | 2/2003 | Eiden et al. |
| 6,519,569 B1 | 2/2003 | White et al. |
| 6,520,930 B2 | 2/2003 | Critchlow et al. |
| 6,540,672 B1 | 4/2003 | Simonsen et al. |
| 6,542,902 B2 | 4/2003 | Dulong et al. |
| 6,544,212 B2 | 4/2003 | Galley et al. |
| 6,544,228 B1 | 4/2003 | Heitmeier |
| 6,546,350 B1 | 4/2003 | Hartmann et al. |
| 6,551,276 B1 | 4/2003 | Mann et al. |
| 6,554,798 B1 | 4/2003 | Mann et al. |
| 6,558,320 B1 | 5/2003 | Causey et al. |
| 6,558,351 B1 | 5/2003 | Steil et al. |
| 6,565,509 B1 | 5/2003 | Say et al. |
| 6,567,416 B1 | 5/2003 | Chuah |
| 6,571,294 B2 | 5/2003 | Simmon et al. |
| 6,572,542 B1 | 6/2003 | Houben et al. |
| 6,572,545 B2 | 6/2003 | Knobbe et al. |
| 6,578,002 B1 | 6/2003 | Derzay et al. |
| 6,581,117 B1 | 6/2003 | Klein et al. |
| 6,587,034 B1 | 7/2003 | Heiman et al. |
| 6,589,229 B1 | 7/2003 | Connelly et al. |
| 6,599,281 B1 | 7/2003 | Struys et al. |

(56) References Cited

U.S. PATENT DOCUMENTS

| | | |
|---|---|---|
| 6,602,191 B2 | 8/2003 | Quy |
| 6,605,072 B2 | 8/2003 | Struys et al. |
| 6,628,809 B1 | 9/2003 | Rowe et al. |
| 6,631,353 B1 | 10/2003 | Davis et al. |
| 6,640,246 B1 | 10/2003 | Gardy, Jr. et al. |
| 6,641,533 B2 | 11/2003 | Causey, III et al. |
| 6,647,299 B2 | 11/2003 | Bourget |
| 6,652,455 B1 | 11/2003 | Kocher |
| 6,653,937 B2 | 11/2003 | Nelson et al. |
| 6,659,947 B1 | 12/2003 | Carter et al. |
| 6,669,630 B1 | 12/2003 | Joliat et al. |
| 6,671,563 B1 | 12/2003 | Engleson et al. |
| 6,673,033 B1 | 1/2004 | Sciulli et al. |
| 6,674,403 B2 | 1/2004 | Gray et al. |
| 6,681,003 B2 | 1/2004 | Linder et al. |
| 6,689,091 B2 | 2/2004 | Bui et al. |
| 6,692,241 B2 | 2/2004 | Watanabe et al. |
| 6,694,191 B2 | 2/2004 | Starkweather et al. |
| 6,694,334 B2 | 2/2004 | DuLong et al. |
| 6,721,286 B1 | 4/2004 | Williams et al. |
| 6,721,582 B2 | 4/2004 | Trepagnier et al. |
| 6,725,200 B1 | 4/2004 | Rost |
| 6,731,989 B2 | 5/2004 | Engleson et al. |
| 6,740,072 B2 | 5/2004 | Starkweather et al. |
| 6,751,651 B2 | 6/2004 | Crockett |
| 6,752,787 B1 | 6/2004 | Causey, III et al. |
| 6,753,830 B2 | 6/2004 | Gelbman |
| 6,758,810 B2 | 7/2004 | Lebel et al. |
| 6,773,396 B2 | 8/2004 | Flach et al. |
| 6,774,786 B1 | 8/2004 | Havekost et al. |
| 6,775,577 B2 | 8/2004 | Cmkovich et al. |
| 6,780,156 B2 | 8/2004 | Haueter et al. |
| 6,790,198 B1 | 9/2004 | White et al. |
| 6,796,956 B2 | 9/2004 | Hartlaub et al. |
| 6,799,149 B2 | 9/2004 | Hartlaub |
| 6,809,653 B1 | 10/2004 | Mann et al. |
| 6,811,534 B2 | 11/2004 | Bowman, IV et al. |
| 6,816,605 B2 | 11/2004 | Rowe et al. |
| 6,839,753 B2 | 1/2005 | Biondi et al. |
| 6,852,104 B2 | 2/2005 | Blomquist |
| 6,859,134 B1 | 2/2005 | Heiman et al. |
| 6,871,211 B2 | 3/2005 | Labounty et al. |
| 6,873,268 B2 | 3/2005 | Lebel et al. |
| 6,876,303 B2 | 4/2005 | Reeder et al. |
| 6,885,881 B2 | 4/2005 | Leonhardt |
| 6,891,525 B2 | 5/2005 | Ogoro |
| 6,892,278 B2 | 5/2005 | Ebergen |
| 6,899,695 B2 | 5/2005 | Herrera |
| 6,915,170 B2 | 7/2005 | Engleson et al. |
| 6,923,763 B1 | 8/2005 | Kovatchev et al. |
| 6,924,781 B1 | 8/2005 | Gelbman |
| 6,928,338 B1 | 8/2005 | Buchser et al. |
| 6,936,029 B2 | 8/2005 | Mann et al. |
| 6,945,954 B2 | 9/2005 | Hochman et al. |
| 6,948,492 B2 | 9/2005 | Wemeling et al. |
| 6,958,677 B1 | 10/2005 | Carter |
| 6,958,691 B1 | 10/2005 | Anderson et al. |
| 6,958,705 B2 | 10/2005 | Lebel et al. |
| 6,961,448 B2 | 11/2005 | Nichols et al. |
| 6,969,352 B2 | 11/2005 | Chiang et al. |
| 6,969,865 B2 | 11/2005 | Duchon et al. |
| 6,974,437 B2 | 12/2005 | Lebel et al. |
| 6,979,326 B2 | 12/2005 | Mann et al. |
| 6,980,958 B1 | 12/2005 | Surwit et al. |
| 6,985,870 B2 | 1/2006 | Martucci et al. |
| 6,986,347 B2 | 1/2006 | Hickle |
| 6,997,880 B2 | 2/2006 | Carlebach et al. |
| 6,997,920 B2 | 2/2006 | Mann et al. |
| 6,998,984 B1 | 2/2006 | Zittrain |
| 7,017,293 B2 | 3/2006 | Riley |
| 7,025,743 B2 | 4/2006 | Mann et al. |
| 7,029,455 B2 | 4/2006 | Flaherty |
| 7,038,584 B2 | 5/2006 | Carter |
| 7,060,031 B2 | 6/2006 | Webb et al. |
| 7,060,059 B2 | 6/2006 | Keith et al. |
| 7,069,552 B2 | 6/2006 | Lindberg et al. |
| 7,072,725 B2 | 7/2006 | Bristol et al. |
| 7,079,035 B2 | 7/2006 | Bock et al. |
| 7,092,943 B2 | 8/2006 | Roese et al. |
| 7,096,072 B2 | 8/2006 | Engleson et al. |
| 7,099,809 B2 | 8/2006 | Dori |
| 7,103,419 B2 | 9/2006 | Engleson et al. |
| 7,103,578 B2 | 9/2006 | Beck et al. |
| 7,107,106 B2 | 9/2006 | Engleson et al. |
| 7,108,680 B2 | 9/2006 | Rohr et al. |
| 7,109,878 B2 | 9/2006 | Mann et al. |
| 7,117,041 B2 | 10/2006 | Engleson et al. |
| 7,136,645 B2 | 11/2006 | Hanson et al. |
| 7,137,964 B2 | 11/2006 | Flaherty |
| 7,142,190 B2 | 11/2006 | Martinez |
| 7,150,741 B2 | 12/2006 | Erickson et al. |
| 7,153,289 B2 | 12/2006 | Vasko |
| 7,154,397 B2 | 12/2006 | Zerhusen et al. |
| 7,156,807 B2 | 1/2007 | Carter et al. |
| 7,161,484 B2 | 1/2007 | Tsoukalis et al. |
| 7,167,755 B2 | 1/2007 | Seeberger et al. |
| 7,167,920 B2 | 1/2007 | Traversat |
| 7,171,277 B2 | 1/2007 | Engleson et al. |
| 7,171,492 B1 | 1/2007 | Borella et al. |
| 7,181,493 B2 | 2/2007 | English et al. |
| 7,185,288 B2 | 2/2007 | McKeever |
| 7,193,514 B2 | 3/2007 | Ritson |
| 7,197,025 B2 | 3/2007 | Chuah |
| 7,201,734 B2 | 4/2007 | Hickle |
| 7,204,823 B2 | 4/2007 | Estes et al. |
| 7,213,009 B2 | 5/2007 | Pestotnik |
| 7,216,802 B1 | 5/2007 | de la Huerga |
| 7,220,240 B2 | 5/2007 | Struys et al. |
| 7,224,979 B2 | 5/2007 | Singhal et al. |
| 7,229,430 B2 | 6/2007 | Hickle et al. |
| 7,230,529 B2 | 6/2007 | Ketcherside |
| 7,236,936 B2 | 6/2007 | White et al. |
| 7,238,164 B2 | 7/2007 | Childers et al. |
| 7,247,154 B2 | 7/2007 | Hickle |
| 7,248,239 B2 | 7/2007 | Dowling |
| 7,250,856 B2 | 7/2007 | Havekost et al. |
| 7,255,683 B2 | 8/2007 | Vanderveen et al. |
| 7,256,888 B2 | 8/2007 | Staehr et al. |
| 7,258,534 B2 | 8/2007 | Fathallah et al. |
| 7,263,213 B2 | 8/2007 | Rowe |
| 7,267,664 B2 | 9/2007 | Rizzo |
| 7,267,665 B2 | 9/2007 | Steil et al. |
| 7,275,156 B2 | 9/2007 | Balfanz et al. |
| 7,278,983 B2 | 10/2007 | Ireland et al. |
| 7,289,815 B2 | 10/2007 | Gfeller et al. |
| 7,289,948 B1 | 10/2007 | Mohri |
| 7,293,107 B1 | 11/2007 | Hanson et al. |
| 7,295,119 B2 | 11/2007 | Rappaport et al. |
| 7,295,556 B2 | 11/2007 | Roese et al. |
| 7,301,451 B2 | 11/2007 | Hastings |
| 7,308,300 B2 | 12/2007 | Toews et al. |
| 7,315,825 B2 | 1/2008 | Rosenfeld et al. |
| 7,319,386 B2 | 1/2008 | Collins, Jr. et al. |
| 7,324,000 B2 | 1/2008 | Zittrain et al. |
| 7,327,705 B2 | 2/2008 | Fletcher et al. |
| 7,343,224 B2 | 3/2008 | DiGianfilippo et al. |
| 7,346,025 B2 | 3/2008 | Bryson |
| 7,347,836 B2 | 3/2008 | Peterson et al. |
| 7,354,420 B2 | 4/2008 | Steil et al. |
| 7,369,897 B2 | 5/2008 | Boveja et al. |
| 7,369,948 B1 | 5/2008 | Ferenczi et al. |
| 7,383,088 B2 | 6/2008 | Spinelli et al. |
| 7,384,410 B2 | 6/2008 | Eggers et al. |
| 7,398,183 B2 | 7/2008 | Holland et al. |
| 7,398,279 B2 | 7/2008 | Muno, Jr. et al. |
| 7,399,277 B2 | 7/2008 | Saidara et al. |
| 7,402,153 B2 | 7/2008 | Steil et al. |
| 7,420,472 B2 | 9/2008 | Tran |
| 7,432,807 B2 | 10/2008 | Schmitt |
| 7,447,643 B1 | 11/2008 | Olson |
| 7,454,314 B2 | 11/2008 | Holland et al. |
| 7,457,804 B2 | 11/2008 | Uber, III et al. |
| 7,464,040 B2 | 12/2008 | Joao |
| 7,471,994 B2 | 12/2008 | Ford et al. |

(56) References Cited

U.S. PATENT DOCUMENTS

| | | |
|---|---|---|
| 7,483,756 B2 | 1/2009 | Engleson et al. |
| 7,489,808 B2 | 2/2009 | Gerder |
| 7,490,021 B2 | 2/2009 | Holland et al. |
| 7,490,048 B2 | 2/2009 | Joao |
| 7,491,187 B2 | 2/2009 | Van Den Berghe et al. |
| 7,519,905 B2 | 4/2009 | Kougiouris et al. |
| 7,523,401 B1 | 4/2009 | Aldridge |
| 7,524,304 B2 | 4/2009 | Genosar |
| 7,551,078 B2 | 6/2009 | Carlson |
| 7,559,321 B2 | 7/2009 | Wermeling et al. |
| 7,565,197 B2 | 7/2009 | Haulbrich et al. |
| 7,572,230 B2 | 8/2009 | Neumann et al. |
| 7,578,802 B2 | 8/2009 | Hickle |
| 7,621,009 B2 | 11/2009 | Elhabashy |
| D606,533 S | 12/2009 | De Jong et al. |
| 7,636,718 B1 | 12/2009 | Steen et al. |
| 7,640,172 B2 | 12/2009 | Kuth |
| 7,645,258 B2 | 1/2010 | White et al. |
| 7,647,237 B2 | 1/2010 | Malave et al. |
| 7,662,124 B2 | 2/2010 | Duchon et al. |
| 7,668,731 B2 | 2/2010 | Martucci et al. |
| 7,671,733 B2 | 3/2010 | McNeal |
| 7,678,071 B2 | 3/2010 | Lebel et al. |
| 7,687,678 B2 | 3/2010 | Jacobs |
| 7,697,994 B2 | 4/2010 | VanDanacker et al. |
| 7,698,239 B2 | 4/2010 | Lieuallen |
| 7,705,727 B2 | 4/2010 | Pestotnik |
| 7,724,147 B2 | 5/2010 | Brown et al. |
| 7,739,126 B1 | 6/2010 | Cave |
| 7,746,218 B2 | 6/2010 | Collins, Jr. |
| 7,766,873 B2 | 8/2010 | Moberg et al. |
| 7,776,029 B2 | 8/2010 | Whitehurst et al. |
| 7,776,031 B2 | 8/2010 | Hartlaub et al. |
| 7,785,313 B2 | 8/2010 | Mastrototaro |
| 7,806,852 B1 | 10/2010 | Jurson |
| 7,806,886 B2 | 10/2010 | Kanderian, Jr. et al. |
| 7,826,981 B2 | 11/2010 | Goode, Jr. et al. |
| 7,835,927 B2 | 11/2010 | Schlotterbeck et al. |
| 7,836,314 B2 | 11/2010 | Chieu |
| 7,856,276 B2 | 12/2010 | Ripart et al. |
| 7,860,583 B2 | 12/2010 | Condurso et al. |
| 7,868,754 B2 | 1/2011 | Salvat, Jr. |
| 7,871,394 B2 | 1/2011 | Halbert et al. |
| 7,886,231 B2 | 2/2011 | Hopermann et al. |
| 7,895,053 B2 | 2/2011 | Holland et al. |
| 7,896,842 B2 | 3/2011 | Palmroos et al. |
| 7,899,546 B2 | 3/2011 | Sieracki et al. |
| 7,905,710 B2 | 3/2011 | Wang et al. |
| 7,920,061 B2 | 4/2011 | Klein et al. |
| 7,933,780 B2 | 4/2011 | de la Huerga |
| 7,938,796 B2 | 5/2011 | Moubayed |
| 7,945,452 B2 | 5/2011 | Fathallah et al. |
| 7,974,714 B2 | 7/2011 | Hoffberg |
| 7,996,241 B2 | 8/2011 | Zak |
| 8,034,026 B2 | 10/2011 | Grant |
| 8,038,593 B2 | 10/2011 | Friedman et al. |
| 8,048,040 B2 | 11/2011 | Kiani |
| 8,060,576 B2 | 11/2011 | Chan et al. |
| 8,065,161 B2 | 11/2011 | Howard et al. |
| 8,066,672 B2 | 11/2011 | Mandro |
| 8,078,983 B2 | 12/2011 | Davis et al. |
| 8,082,018 B2 | 12/2011 | Duchon et al. |
| 8,082,312 B2 | 12/2011 | Chan et al. |
| 8,147,448 B2 | 4/2012 | Sundar et al. |
| 8,149,131 B2 | 4/2012 | Blomquist |
| 8,169,914 B2 | 5/2012 | Bajpai |
| 8,171,094 B2 | 5/2012 | Chan et al. |
| 8,172,798 B2 | 5/2012 | Hungerford et al. |
| 8,185,322 B2 | 5/2012 | Schroeder et al. |
| 8,195,478 B2 | 6/2012 | Petersen et al. |
| 8,206,350 B2 | 6/2012 | Mann et al. |
| 8,219,413 B2 | 7/2012 | Martinez et al. |
| 8,231,578 B2 | 7/2012 | Fathallah et al. |
| 8,234,128 B2 | 7/2012 | Martucci et al. |
| 8,267,892 B2 | 9/2012 | Spencer et al. |
| 8,271,106 B2 | 9/2012 | Wehba et al. |
| 8,287,495 B2 | 10/2012 | Michaud et al. |
| 8,291,337 B2 | 10/2012 | Gannin et al. |
| 8,298,184 B2 | 10/2012 | DiPerna et al. |
| 8,352,290 B2 | 1/2013 | Bartz et al. |
| 8,359,338 B2 | 1/2013 | Butterfield et al. |
| 8,380,536 B2 | 2/2013 | Howard et al. |
| 8,387,112 B1 | 2/2013 | Ranjan et al. |
| 8,394,077 B2 | 3/2013 | Jacobson et al. |
| 8,403,908 B2 | 3/2013 | Jacobson et al. |
| 8,435,206 B2 | 5/2013 | Evans et al. |
| 8,449,523 B2 | 5/2013 | Brukalo et al. |
| 8,452,953 B2 | 5/2013 | Buck et al. |
| 8,453,645 B2 | 6/2013 | Figueiredo et al. |
| 8,480,648 B2 | 7/2013 | Burnett et al. |
| 8,489,427 B2 | 7/2013 | Simpson et al. |
| 8,494,879 B2 | 7/2013 | Davis et al. |
| 8,504,179 B2 | 8/2013 | Blomquist |
| 8,517,990 B2 | 8/2013 | Teel et al. |
| 8,518,021 B2 | 8/2013 | Stewart et al. |
| 8,543,416 B2 | 9/2013 | Palmroos et al. |
| 8,551,038 B2 | 10/2013 | Tsoukalis et al. |
| 8,560,345 B2 | 10/2013 | Wehba et al. |
| 8,577,692 B2 | 11/2013 | Silkaitis et al. |
| 8,579,884 B2 | 11/2013 | Lanier et al. |
| 8,626,530 B1 | 1/2014 | Tran et al. |
| 8,655,676 B2 | 2/2014 | Wehba et al. |
| 8,660,860 B2 | 2/2014 | Wehba et al. |
| 8,662,388 B2 | 3/2014 | Belkin |
| 8,666,769 B2 | 3/2014 | Butler et al. |
| 8,700,421 B2 | 4/2014 | Feng et al. |
| 8,731,960 B2 | 5/2014 | Butler et al. |
| 8,768,719 B2 | 7/2014 | Wehba et al. |
| 8,771,251 B2 | 7/2014 | Ruchti et al. |
| 8,777,894 B2 | 7/2014 | Butterfield et al. |
| 8,777,895 B2 | 7/2014 | Hsu et al. |
| 8,799,012 B2 | 8/2014 | Butler et al. |
| 8,876,793 B2 | 11/2014 | Ledford et al. |
| 8,922,330 B2 | 12/2014 | Moberg et al. |
| 8,936,565 B2 | 1/2015 | Chawla |
| 8,952,794 B2 | 2/2015 | Bloomquist et al. |
| 8,998,100 B2 | 4/2015 | Halbert et al. |
| 9,026,370 B2 | 5/2015 | Rubalcaba et al. |
| 9,069,887 B2 | 6/2015 | Gupta et al. |
| 9,089,642 B2 | 7/2015 | Murphy et al. |
| 9,114,217 B2 | 8/2015 | Sur et al. |
| 9,123,077 B2 | 9/2015 | Silkaitis et al. |
| 9,192,712 B2 | 11/2015 | DeBelser et al. |
| 9,240,002 B2 | 1/2016 | Hume et al. |
| 9,381,296 B2 | 7/2016 | Arrizza et al. |
| 9,393,362 B2 | 7/2016 | Cozmi et al. |
| 9,498,583 B2 | 11/2016 | Sur et al. |
| 9,539,383 B2 | 1/2017 | Kohlbrecher |
| 9,572,923 B2 | 2/2017 | Howard et al. |
| 9,594,875 B2 | 3/2017 | Arrizza et al. |
| 9,604,000 B2 | 3/2017 | Wehba et al. |
| 9,641,432 B2 | 5/2017 | Jha et al. |
| 9,649,431 B2 | 5/2017 | Gray et al. |
| 9,662,436 B2 | 5/2017 | Belkin et al. |
| 9,690,909 B2 | 6/2017 | Stewart et al. |
| 9,707,341 B2 | 7/2017 | Dumas, III et al. |
| 9,724,470 B2 | 8/2017 | Day et al. |
| 9,764,082 B2 | 9/2017 | Day et al. |
| 9,971,871 B2 | 5/2018 | Arrizza et al. |
| 9,995,611 B2 | 6/2018 | Ruchti et al. |
| 10,022,498 B2 | 7/2018 | Ruchti et al. |
| 10,042,986 B2 | 8/2018 | Ruchti et al. |
| 10,046,112 B2 | 8/2018 | Oruklu et al. |
| 10,166,328 B2 | 1/2019 | Oruklu et al. |
| 10,238,799 B2 | 3/2019 | Kohlbrecher |
| 10,238,801 B2 | 3/2019 | Wehba et al. |
| 10,242,060 B2 | 3/2019 | Butler et al. |
| 10,300,194 B2 | 5/2019 | Day et al. |
| 10,311,972 B2 | 6/2019 | Kohlbrecher et al. |
| 10,314,974 B2 | 6/2019 | Day et al. |
| 10,333,843 B2 | 6/2019 | Jha et al. |
| 10,430,761 B2 | 10/2019 | Hume et al. |
| 10,434,246 B2 | 10/2019 | Silkaitis et al. |
| 10,463,788 B2 | 11/2019 | Day |

(56) References Cited

U.S. PATENT DOCUMENTS

| | | |
|---|---|---|
| 2001/0016056 A1 | 8/2001 | Westphal et al. |
| 2001/0031944 A1 | 10/2001 | Peterson et al. |
| 2001/0032099 A1 | 10/2001 | Joao |
| 2001/0037060 A1 | 11/2001 | Thompson et al. |
| 2001/0044731 A1 | 11/2001 | Coffman et al. |
| 2001/0048027 A1 | 12/2001 | Walsh |
| 2001/0051787 A1 | 12/2001 | Haller et al. |
| 2001/0056358 A1 | 12/2001 | Dulong et al. |
| 2002/0010595 A1 | 1/2002 | Kapp |
| 2002/0013723 A1 | 1/2002 | Mise |
| 2002/0015018 A1 | 2/2002 | Shimazu et al. |
| 2002/0019584 A1 | 2/2002 | Schulze et al. |
| 2002/0026103 A1 | 2/2002 | Norris et al. |
| 2002/0029776 A1 | 3/2002 | Blomquist |
| 2002/0032583 A1 | 3/2002 | Joao |
| 2002/0040208 A1 | 4/2002 | Flaherty et al. |
| 2002/0040282 A1 | 4/2002 | Bailey et al. |
| 2002/0082728 A1 | 6/2002 | Mueller et al. |
| 2002/0087115 A1 | 7/2002 | Hartlaub |
| 2002/0087116 A1 | 7/2002 | Hartlaub |
| 2002/0095486 A1 | 7/2002 | Bahl |
| 2002/0103675 A1 | 8/2002 | Vanelli |
| 2002/0123905 A1 | 9/2002 | Goodroe et al. |
| 2002/0143580 A1 | 10/2002 | Bristol et al. |
| 2002/0152239 A1 | 10/2002 | Bautista-Lloyd et al. |
| 2002/0173702 A1* | 11/2002 | Lebel ............... A61N 1/37264 600/300 |
| 2002/0173875 A1 | 11/2002 | Wallace et al. |
| 2002/0194329 A1 | 12/2002 | Ailing |
| 2003/0009244 A1 | 1/2003 | Engleson |
| 2003/0013959 A1 | 1/2003 | Grunwald et al. |
| 2003/0014222 A1 | 1/2003 | Klass et al. |
| 2003/0014817 A1 | 1/2003 | Gallant et al. |
| 2003/0025602 A1 | 2/2003 | Medema et al. |
| 2003/0028082 A1 | 2/2003 | Thompson |
| 2003/0036683 A1 | 2/2003 | Kehr et al. |
| 2003/0047126 A1 | 3/2003 | Tomaschko |
| 2003/0050621 A1 | 3/2003 | Lebel et al. |
| 2003/0059750 A1 | 3/2003 | Bindler et al. |
| 2003/0060688 A1 | 3/2003 | Ciarniello et al. |
| 2003/0069963 A1 | 4/2003 | Jayant et al. |
| 2003/0079746 A1 | 5/2003 | Hickle |
| 2003/0097529 A1 | 5/2003 | Arimilli et al. |
| 2003/0104982 A1 | 6/2003 | Wittmann et al. |
| 2003/0106553 A1 | 6/2003 | Vanderveen |
| 2003/0115358 A1 | 6/2003 | Yun |
| 2003/0120384 A1 | 6/2003 | Haitin et al. |
| 2003/0125662 A1 | 7/2003 | Bui |
| 2003/0130616 A1 | 7/2003 | Steil |
| 2003/0135087 A1 | 7/2003 | Hickle et al. |
| 2003/0139701 A1 | 7/2003 | White et al. |
| 2003/0140928 A1 | 7/2003 | Bui et al. |
| 2003/0140929 A1 | 7/2003 | Wilkes et al. |
| 2003/0141981 A1 | 7/2003 | Bui et al. |
| 2003/0143746 A1 | 7/2003 | Sage, Jr. |
| 2003/0144878 A1 | 7/2003 | Wilkes et al. |
| 2003/0158749 A1 | 8/2003 | Olchanski et al. |
| 2003/0187338 A1 | 10/2003 | Say et al. |
| 2003/0200116 A1 | 10/2003 | Forrester |
| 2003/0204416 A1 | 10/2003 | Acharya |
| 2003/0204781 A1 | 10/2003 | Peebles et al. |
| 2003/0212364 A1 | 11/2003 | Mann et al. |
| 2003/0212379 A1 | 11/2003 | Bylund et al. |
| 2003/0212821 A1 | 11/2003 | Gillies et al. |
| 2003/0217962 A1 | 11/2003 | Childers et al. |
| 2004/0015132 A1 | 1/2004 | Brown |
| 2004/0019607 A1 | 1/2004 | Moubayed et al. |
| 2004/0030323 A1 | 2/2004 | Ullestad et al. |
| 2004/0039257 A1 | 2/2004 | Hickle |
| 2004/0057226 A1 | 3/2004 | Berthou et al. |
| 2004/0064341 A1 | 4/2004 | Langan et al. |
| 2004/0064342 A1 | 4/2004 | Browne et al. |
| 2004/0064435 A1 | 4/2004 | Moubayed et al. |
| 2004/0073811 A1 | 4/2004 | Sanin |
| 2004/0077934 A1 | 4/2004 | Massad |
| 2004/0078231 A1 | 4/2004 | Wilkes et al. |
| 2004/0078236 A1 | 4/2004 | Stoodley et al. |
| 2004/0104271 A1 | 6/2004 | Martucci et al. |
| 2004/0122530 A1 | 6/2004 | Hansen |
| 2004/0128162 A1 | 7/2004 | Schlotterbeck et al. |
| 2004/0128163 A1 | 7/2004 | Goodman et al. |
| 2004/0133441 A1 | 7/2004 | Brady et al. |
| 2004/0145480 A1 | 7/2004 | Despotis |
| 2004/0147034 A1 | 7/2004 | Gore et al. |
| 2004/0167464 A1 | 8/2004 | Ireland et al. |
| 2004/0167465 A1 | 8/2004 | Kohler |
| 2004/0167804 A1 | 8/2004 | Simpson |
| 2004/0172222 A1 | 9/2004 | Simpson et al. |
| 2004/0172283 A1 | 9/2004 | Vanderveen |
| 2004/0172301 A1 | 9/2004 | Mihai et al. |
| 2004/0172302 A1 | 9/2004 | Martucci et al. |
| 2004/0176667 A1 | 9/2004 | Mihai et al. |
| 2004/0176980 A1 | 9/2004 | Bulitta et al. |
| 2004/0176984 A1 | 9/2004 | White et al. |
| 2004/0181314 A1 | 9/2004 | Zaleski |
| 2004/0189708 A1 | 9/2004 | Larcheveque et al. |
| 2004/0193325 A1 | 9/2004 | Bonderud |
| 2004/0193328 A1 | 9/2004 | Butterfield et al. |
| 2004/0193453 A1 | 9/2004 | Butterfield et al. |
| 2004/0204673 A1 | 10/2004 | Flaherty et al. |
| 2004/0215278 A1 | 10/2004 | Stegink et al. |
| 2004/0220517 A1 | 11/2004 | Starkweather et al. |
| 2004/0225252 A1 | 11/2004 | Gillespie et al. |
| 2004/0236240 A1 | 11/2004 | Kraus et al. |
| 2004/0243438 A1 | 12/2004 | Mintz |
| 2004/0254434 A1 | 12/2004 | Goodnow et al. |
| 2005/0010269 A1 | 1/2005 | Lebel et al. |
| 2005/0020886 A1 | 1/2005 | Hutchinson et al. |
| 2005/0021006 A1 | 1/2005 | Tonnies |
| 2005/0027560 A1 | 2/2005 | Cook |
| 2005/0027567 A1 | 2/2005 | Taha |
| 2005/0038311 A1 | 2/2005 | Kuth |
| 2005/0038669 A1 | 2/2005 | Sachdeva et al. |
| 2005/0038680 A1 | 2/2005 | McMahon |
| 2005/0040226 A1 | 2/2005 | Al-Sheikh |
| 2005/0043620 A1 | 2/2005 | Fallows et al. |
| 2005/0049910 A1 | 3/2005 | Lancaster et al. |
| 2005/0055242 A1 | 3/2005 | Bello et al. |
| 2005/0055244 A1 | 3/2005 | Mullan et al. |
| 2005/0065465 A1 | 3/2005 | Lebel et al. |
| 2005/0065817 A1 | 3/2005 | Mihai et al. |
| 2005/0075544 A1 | 4/2005 | Shapiro et al. |
| 2005/0080801 A1 | 4/2005 | Kothandaraman et al. |
| 2005/0086071 A1 | 4/2005 | Fox, Jr. et al. |
| 2005/0086072 A1 | 4/2005 | Fox |
| 2005/0090808 A1 | 4/2005 | Malave et al. |
| 2005/0099624 A1 | 5/2005 | Staehr |
| 2005/0102162 A1 | 5/2005 | Blumenfeld |
| 2005/0102165 A1 | 5/2005 | Oshita et al. |
| 2005/0102167 A1 | 5/2005 | Kapoor |
| 2005/0102669 A1 | 5/2005 | Marney et al. |
| 2005/0107923 A1 | 5/2005 | Vanderveen |
| 2005/0117529 A1 | 6/2005 | Ramos-Escano |
| 2005/0119788 A1 | 6/2005 | Engleson et al. |
| 2005/0119914 A1 | 6/2005 | Batch |
| 2005/0131739 A1 | 6/2005 | Rabinowitz et al. |
| 2005/0137522 A1 | 6/2005 | Aoki |
| 2005/0137573 A1 | 6/2005 | McLaughlin |
| 2005/0154769 A1 | 7/2005 | Eckart et al. |
| 2005/0160057 A1 | 7/2005 | Wefers et al. |
| 2005/0171503 A1 | 8/2005 | Van Den Berghe et al. |
| 2005/0171815 A1 | 8/2005 | Vanderveen |
| 2005/0177096 A1 | 8/2005 | Bollish et al. |
| 2005/0177395 A1 | 8/2005 | Blomquist |
| 2005/0182306 A1 | 8/2005 | Sloan |
| 2005/0182355 A1 | 8/2005 | Bui |
| 2005/0187950 A1 | 8/2005 | Parker |
| 2005/0192557 A1 | 9/2005 | Brauker et al. |
| 2005/0197554 A1 | 9/2005 | Polcha |
| 2005/0197621 A1 | 9/2005 | Poulsen et al. |
| 2005/0210037 A1 | 9/2005 | Wefers et al. |
| 2005/0216479 A1 | 9/2005 | Wefers et al. |
| 2005/0216480 A1 | 9/2005 | Wefers et al. |
| 2005/0223045 A1 | 10/2005 | Funahashi et al. |

(56) References Cited

U.S. PATENT DOCUMENTS

| | | |
|---|---|---|
| 2005/0224083 A1 | 10/2005 | Crass |
| 2005/0234746 A1 | 10/2005 | Funahashi |
| 2005/0240305 A1 | 10/2005 | Bogash et al. |
| 2005/0246416 A1 | 11/2005 | Blomquist |
| 2005/0251418 A1 | 11/2005 | Fox, Jr. et al. |
| 2005/0273059 A1 | 12/2005 | Mernoe et al. |
| 2005/0277873 A1 | 12/2005 | Stewart et al. |
| 2005/0277890 A1 | 12/2005 | Stewart et al. |
| 2005/0277911 A1 | 12/2005 | Stewart et al. |
| 2005/0278194 A1 | 12/2005 | Holland et al. |
| 2006/0004772 A1 | 1/2006 | Hagan et al. |
| 2006/0009727 A1 | 1/2006 | O'Mahony et al. |
| 2006/0009734 A1 | 1/2006 | Martin |
| 2006/0010098 A1 | 1/2006 | Goodnow et al. |
| 2006/0042139 A1 | 3/2006 | Mendes |
| 2006/0047270 A1 | 3/2006 | Shelton |
| 2006/0053036 A1 | 3/2006 | Coffman et al. |
| 2006/0064020 A1 | 3/2006 | Burnes et al. |
| 2006/0074633 A1 | 4/2006 | Mahesh et al. |
| 2006/0074920 A1 | 4/2006 | Wefers et al. |
| 2006/0079831 A1 | 4/2006 | Gilbert |
| 2006/0089854 A1 | 4/2006 | Holland et al. |
| 2006/0089855 A1 | 4/2006 | Holland et al. |
| 2006/0100746 A1 | 5/2006 | Leibner-Druska |
| 2006/0100907 A1 | 5/2006 | Holland et al. |
| 2006/0106649 A1 | 5/2006 | Eggers et al. |
| 2006/0111943 A1 | 5/2006 | Wu |
| 2006/0116904 A1 | 6/2006 | Brem |
| 2006/0116907 A1 | 6/2006 | Rhodes et al. |
| 2006/0122481 A1 | 6/2006 | Sievenpiper et al. |
| 2006/0122867 A1 | 6/2006 | Eggers et al. |
| 2006/0129429 A1 | 6/2006 | Moubayed et al. |
| 2006/0129434 A1 | 6/2006 | Smitherman et al. |
| 2006/0129435 A1 | 6/2006 | Smitherman et al. |
| 2006/0136266 A1 | 6/2006 | Tarassenko et al. |
| 2006/0136271 A1 | 6/2006 | Eggers et al. |
| 2006/0143051 A1 | 6/2006 | Eggers et al. |
| 2006/0173260 A1 | 8/2006 | Gaoni et al. |
| 2006/0173406 A1 | 8/2006 | Hayes et al. |
| 2006/0173715 A1 | 8/2006 | Wang et al. |
| 2006/0173927 A1 | 8/2006 | Beyer et al. |
| 2006/0190302 A1 | 8/2006 | Eggers et al. |
| 2006/0195022 A1 | 8/2006 | Trepagnier et al. |
| 2006/0200007 A1 | 9/2006 | Brockway et al. |
| 2006/0200369 A1 | 9/2006 | Batch et al. |
| 2006/0211404 A1 | 9/2006 | Cromp et al. |
| 2006/0224141 A1 | 10/2006 | Rush et al. |
| 2006/0229918 A1 | 10/2006 | Fotsch et al. |
| 2006/0258985 A1 | 11/2006 | Russell |
| 2006/0259327 A1 | 11/2006 | Hoag |
| 2006/0264895 A1 | 11/2006 | Flanders |
| 2006/0265246 A1 | 11/2006 | Hoag |
| 2006/0267753 A1 | 11/2006 | Hussey et al. |
| 2006/0268710 A1 | 11/2006 | Appanna et al. |
| 2006/0277206 A1 | 12/2006 | Bailey et al. |
| 2006/0287885 A1 | 12/2006 | Frick |
| 2007/0015972 A1 | 1/2007 | Wang et al. |
| 2007/0016443 A1 | 1/2007 | Wachman et al. |
| 2007/0027506 A1 | 2/2007 | Stender et al. |
| 2007/0060796 A1 | 3/2007 | Kim |
| 2007/0060870 A1 | 3/2007 | Tolle et al. |
| 2007/0060871 A1 | 3/2007 | Istoc |
| 2007/0061393 A1 | 3/2007 | Moore |
| 2007/0065363 A1 | 3/2007 | Dalal et al. |
| 2007/0073419 A1 | 3/2007 | Sesay |
| 2007/0078314 A1 | 4/2007 | Grounsell |
| 2007/0083870 A1 | 4/2007 | Kanakogi |
| 2007/0088333 A1 | 4/2007 | Levin et al. |
| 2007/0093786 A1 | 4/2007 | Goldsmith et al. |
| 2007/0100665 A1 | 5/2007 | Brown |
| 2007/0100667 A1 | 5/2007 | Bardy |
| 2007/0106126 A1 | 5/2007 | Mannheimer et al. |
| 2007/0112298 A1 | 5/2007 | Mueller et al. |
| 2007/0116037 A1 | 5/2007 | Moore |
| 2007/0118405 A1 | 5/2007 | Campbell et al. |
| 2007/0135866 A1 | 6/2007 | Baker |
| 2007/0136098 A1 | 6/2007 | Smythe et al. |
| 2007/0142822 A1 | 6/2007 | Remde |
| 2007/0156282 A1 | 7/2007 | Dunn |
| 2007/0156452 A1 | 7/2007 | Batch |
| 2007/0169008 A1 | 7/2007 | Varanasi et al. |
| 2007/0179448 A1 | 8/2007 | Lim et al. |
| 2007/0186923 A1 | 8/2007 | Poutiatine et al. |
| 2007/0191817 A1 | 8/2007 | Martin |
| 2007/0191973 A1 | 8/2007 | Holzbauer et al. |
| 2007/0213657 A1 | 9/2007 | Jennewine et al. |
| 2007/0214003 A1 | 9/2007 | Holland et al. |
| 2007/0215545 A1 | 9/2007 | Bissler et al. |
| 2007/0229249 A1 | 10/2007 | McNeal et al. |
| 2007/0232867 A1 | 10/2007 | Hansmann |
| 2007/0233035 A1 | 10/2007 | Wehba et al. |
| 2007/0233049 A1 | 10/2007 | Wehba et al. |
| 2007/0233206 A1 | 10/2007 | Frikart |
| 2007/0233520 A1 | 10/2007 | Wehba et al. |
| 2007/0251835 A1 | 11/2007 | Mehta et al. |
| 2007/0253021 A1 | 11/2007 | Mehta et al. |
| 2007/0254593 A1 | 11/2007 | Jollota et al. |
| 2007/0255125 A1 | 11/2007 | Moberg et al. |
| 2007/0257788 A1 | 11/2007 | Carlson |
| 2007/0258395 A1 | 11/2007 | Jollota et al. |
| 2007/0299687 A1 | 12/2007 | Palmer et al. |
| 2007/0299695 A1 | 12/2007 | Jung et al. |
| 2008/0004904 A1 | 1/2008 | Tran |
| 2008/0009684 A1 | 1/2008 | Corsetti et al. |
| 2008/0033361 A1 | 2/2008 | Evans et al. |
| 2008/0034323 A1 | 2/2008 | Blomquist |
| 2008/0041942 A1 | 2/2008 | Aissa |
| 2008/0052704 A1 | 2/2008 | Wysocki |
| 2008/0065007 A1 | 3/2008 | Peterson et al. |
| 2008/0065417 A1 | 3/2008 | Jung et al. |
| 2008/0071217 A1 | 3/2008 | Moubayed et al. |
| 2008/0071251 A1 | 3/2008 | Moubayed et al. |
| 2008/0091466 A1 | 4/2008 | Butler et al. |
| 2008/0095339 A1 | 4/2008 | Elliott |
| 2008/0097289 A1 | 4/2008 | Steil et al. |
| 2008/0126969 A1 | 5/2008 | Blomquist |
| 2008/0139907 A1 | 6/2008 | Rao et al. |
| 2008/0147145 A1 | 6/2008 | Sieracki et al. |
| 2008/0149117 A1 | 6/2008 | Raghuram |
| 2008/0154177 A1 | 6/2008 | Moubayed et al. |
| 2008/0172337 A1 | 7/2008 | Banfield et al. |
| 2008/0184219 A1 | 7/2008 | Matsumoto |
| 2008/0188796 A1 | 8/2008 | Steil et al. |
| 2008/0214919 A1 | 9/2008 | Harmon et al. |
| 2008/0246748 A1 | 10/2008 | Cassidy et al. |
| 2008/0256305 A1 | 10/2008 | Kwon |
| 2008/0262469 A1 | 10/2008 | Bristol et al. |
| 2008/0269714 A1 | 10/2008 | Mastrototaro et al. |
| 2008/0269723 A1 | 10/2008 | Mastrototaro et al. |
| 2008/0275384 A1 | 11/2008 | Mastrototaro et al. |
| 2008/0300572 A1 | 12/2008 | Rankers et al. |
| 2008/0320387 A1 | 12/2008 | Sasaki et al. |
| 2008/0320466 A1 | 12/2008 | Dias |
| 2009/0005703 A1 | 1/2009 | Fasciano |
| 2009/0005728 A1 | 1/2009 | Weinert et al. |
| 2009/0006061 A1 | 1/2009 | Thukral et al. |
| 2009/0006129 A1 | 1/2009 | Thukral |
| 2009/0006133 A1 | 1/2009 | Weinert |
| 2009/0018495 A1 | 1/2009 | Panduro |
| 2009/0051560 A1 | 2/2009 | Manning et al. |
| 2009/0054743 A1 | 2/2009 | Stewart |
| 2009/0054754 A1 | 2/2009 | McMahon et al. |
| 2009/0057399 A1 | 3/2009 | Sajkowsky |
| 2009/0069785 A1 | 3/2009 | Miller et al. |
| 2009/0099867 A1 | 4/2009 | Newman |
| 2009/0135196 A1 | 5/2009 | Holland et al. |
| 2009/0143662 A1 | 6/2009 | Estes et al. |
| 2009/0149743 A1 | 6/2009 | Barron et al. |
| 2009/0150174 A1 | 6/2009 | Buck et al. |
| 2009/0150878 A1 | 6/2009 | Pathak et al. |
| 2009/0156991 A1 | 6/2009 | Roberts |
| 2009/0157695 A1 | 6/2009 | Roberts |
| 2009/0158274 A1 | 6/2009 | Roberts |
| 2009/0177146 A1 | 7/2009 | Nesbitt et al. |

(56) References Cited

U.S. PATENT DOCUMENTS

| | | |
|---|---|---|
| 2009/0177769 A1 | 7/2009 | Roberts |
| 2009/0177992 A1 | 7/2009 | Rubalcaba et al. |
| 2009/0183147 A1 | 7/2009 | Davis et al. |
| 2009/0209938 A1 | 8/2009 | Aalto-Setala |
| 2009/0210250 A1 | 8/2009 | Prax et al. |
| 2009/0221890 A1 | 9/2009 | Saffer et al. |
| 2009/0231249 A1 | 9/2009 | Wang et al. |
| 2009/0270833 A1 | 10/2009 | DeBelser |
| 2009/0275886 A1 | 11/2009 | Bloomquist et al. |
| 2009/0275896 A1 | 11/2009 | Kamen et al. |
| 2009/0284691 A1 | 11/2009 | Marhefka et al. |
| 2009/0326340 A1 | 12/2009 | Wang |
| 2009/0326516 A1 | 12/2009 | Bangera et al. |
| 2010/0022988 A1 | 1/2010 | Wochner |
| 2010/0036310 A1 | 2/2010 | Hillman |
| 2010/0056992 A1 | 3/2010 | Hayter |
| 2010/0095229 A1 | 4/2010 | Dixon et al. |
| 2010/0121170 A1 | 5/2010 | Rule |
| 2010/0121415 A1 | 5/2010 | Skelton et al. |
| 2010/0121654 A1 | 5/2010 | Portnoy et al. |
| 2010/0121752 A1 | 5/2010 | Banigan et al. |
| 2010/0130933 A1 | 5/2010 | Holland et al. |
| 2010/0131434 A1 | 5/2010 | Magent et al. |
| 2010/0138523 A1 | 6/2010 | Umess et al. |
| 2010/0146137 A1 | 6/2010 | Wu et al. |
| 2010/0156633 A1 | 6/2010 | Buck et al. |
| 2010/0160854 A1 | 6/2010 | Gauthier |
| 2010/0160860 A1 | 6/2010 | Celentano et al. |
| 2010/0174266 A1 | 7/2010 | Estes |
| 2010/0191525 A1 | 7/2010 | Rabenko et al. |
| 2010/0198034 A1 | 8/2010 | Thomas et al. |
| 2010/0198196 A1 | 8/2010 | Wei |
| 2010/0200506 A1 | 8/2010 | Ware et al. |
| 2010/0204574 A1 | 8/2010 | Duchon et al. |
| 2010/0209268 A1 | 8/2010 | Davis |
| 2010/0212675 A1 | 8/2010 | Walling et al. |
| 2010/0217621 A1 | 8/2010 | Schoenberg |
| 2010/0234708 A1 | 9/2010 | Buck et al. |
| 2010/0250732 A1 | 9/2010 | Bucknell |
| 2010/0271479 A1 | 10/2010 | Heydlauf |
| 2010/0273738 A1 | 10/2010 | Valcke et al. |
| 2010/0280486 A1 | 11/2010 | Khair et al. |
| 2010/0292634 A1 | 11/2010 | Kircher |
| 2010/0298765 A1 | 11/2010 | Budiman et al. |
| 2010/0318025 A1 | 12/2010 | John |
| 2011/0001605 A1 | 1/2011 | Kiani et al. |
| 2011/0040158 A1 | 2/2011 | Katz et al. |
| 2011/0060758 A1 | 3/2011 | Schlotterbeck et al. |
| 2011/0071844 A1 | 3/2011 | Cannon et al. |
| 2011/0072379 A1 | 3/2011 | Gannon |
| 2011/0078608 A1 | 3/2011 | Gannon et al. |
| 2011/0093284 A1 | 4/2011 | Dicks et al. |
| 2011/0099313 A1 | 4/2011 | Bolanowski |
| 2011/0125095 A1 | 5/2011 | Lebel et al. |
| 2011/0138185 A1 | 6/2011 | Ju et al. |
| 2011/0175728 A1 | 7/2011 | Baker, Jr. |
| 2011/0178462 A1 | 7/2011 | Moberg et al. |
| 2011/0196748 A1 | 8/2011 | Caron et al. |
| 2011/0231216 A1 | 9/2011 | Fyke et al. |
| 2011/0257496 A1 | 10/2011 | Terashima et al. |
| 2011/0257798 A1 | 10/2011 | Ali et al. |
| 2011/0259954 A1 | 10/2011 | Bartz et al. |
| 2011/0264043 A1 | 10/2011 | Kotnick et al. |
| 2011/0264044 A1 | 10/2011 | Bartz et al. |
| 2011/0266221 A1 | 11/2011 | Ware et al. |
| 2011/0270045 A1 | 11/2011 | Lebel et al. |
| 2011/0275904 A1 | 11/2011 | Lebel et al. |
| 2011/0286457 A1 | 11/2011 | Ee |
| 2011/0289497 A1 | 11/2011 | Kiaie et al. |
| 2011/0295196 A1 | 12/2011 | Chazot et al. |
| 2011/0295341 A1 | 12/2011 | Estes et al. |
| 2011/0296051 A1 | 12/2011 | Vange |
| 2011/0296411 A1 | 12/2011 | Tang et al. |
| 2011/0313789 A1 | 12/2011 | Karmen et al. |
| 2011/0319813 A1 | 12/2011 | Kamen et al. |
| 2011/0320049 A1 | 12/2011 | Chossat et al. |
| 2012/0005680 A1 | 1/2012 | Dolby et al. |
| 2012/0011253 A1 | 1/2012 | Friedman et al. |
| 2012/0016305 A1 | 1/2012 | Jollota |
| 2012/0029941 A1 | 2/2012 | Malave et al. |
| 2012/0065990 A1 | 3/2012 | Howard et al. |
| 2012/0066609 A1 | 3/2012 | Howard et al. |
| 2012/0070045 A1 | 3/2012 | Vesper et al. |
| 2012/0095437 A1 | 4/2012 | Hemmerling |
| 2012/0112903 A1 | 5/2012 | Kaib et al. |
| 2012/0130198 A1 | 5/2012 | Beaule |
| 2012/0143116 A1 | 6/2012 | Ware et al. |
| 2012/0150556 A1 | 6/2012 | Galasso et al. |
| 2012/0172802 A1 | 7/2012 | Blomquist |
| 2012/0179135 A1 | 7/2012 | Rinehart et al. |
| 2012/0179136 A1 | 7/2012 | Rinehart et al. |
| 2012/0203177 A1 | 8/2012 | Lanier |
| 2012/0245554 A1 | 9/2012 | Kawamura |
| 2012/0259978 A1 | 10/2012 | Petersen et al. |
| 2012/0277716 A1 | 11/2012 | Ali et al. |
| 2012/0284734 A1 | 11/2012 | McQuaid et al. |
| 2012/0323212 A1 | 12/2012 | Murphy |
| 2013/0006666 A1 | 1/2013 | Schneider |
| 2013/0006702 A1 | 1/2013 | Wu |
| 2013/0012880 A1 | 1/2013 | Blomquist |
| 2013/0015980 A1 | 1/2013 | Evans et al. |
| 2013/0036403 A1 | 2/2013 | Geist |
| 2013/0036412 A1 | 2/2013 | Birtwhistle et al. |
| 2013/0066265 A1 | 3/2013 | Grant |
| 2013/0072872 A1 | 3/2013 | Yodfat et al. |
| 2013/0096444 A1 | 4/2013 | Condurso et al. |
| 2013/0096648 A1 | 4/2013 | Benson |
| 2013/0102963 A1 | 4/2013 | Marsh et al. |
| 2013/0138452 A1 | 5/2013 | Cork et al. |
| 2013/0144206 A1 | 6/2013 | Lee et al. |
| 2013/0167245 A1 | 6/2013 | Birtwhistle et al. |
| 2013/0191770 A1 | 7/2013 | Bartz et al. |
| 2013/0204188 A1 | 8/2013 | Kamen et al. |
| 2013/0218080 A1 | 8/2013 | Peterfreund et al. |
| 2013/0274669 A1 | 10/2013 | Stempfle et al. |
| 2013/0275539 A1 | 10/2013 | Gross et al. |
| 2013/0291116 A1 | 10/2013 | Homer |
| 2013/0296823 A1 | 11/2013 | Melker et al. |
| 2013/0296984 A1 | 11/2013 | Burnett et al. |
| 2013/0317753 A1 | 11/2013 | Kamen et al. |
| 2013/0346108 A1 | 12/2013 | Kamen et al. |
| 2014/0039446 A1 | 2/2014 | Day |
| 2014/0163517 A1 | 6/2014 | Finan et al. |
| 2014/0180711 A1 | 6/2014 | Kamen et al. |
| 2014/0257251 A1 | 9/2014 | Bush et al. |
| 2014/0266790 A1 | 9/2014 | Al-Ali et al. |
| 2014/0269643 A1 | 9/2014 | Sun |
| 2014/0288947 A1 | 9/2014 | Simpson et al. |
| 2014/0297329 A1 | 10/2014 | Rock |
| 2014/0350513 A1 | 11/2014 | Oruklu et al. |
| 2014/0358077 A1 | 12/2014 | Oruklu et al. |
| 2014/0366878 A1 | 12/2014 | Baron |
| 2015/0005935 A1 | 1/2015 | Bae et al. |
| 2015/0058044 A1 | 2/2015 | Butler et al. |
| 2015/0066531 A1 | 3/2015 | Jacobson et al. |
| 2015/0100038 A1 | 4/2015 | McCann et al. |
| 2015/0134265 A1 | 5/2015 | Kohlbrecher et al. |
| 2015/0141955 A1 | 5/2015 | Ruchti et al. |
| 2015/0151051 A1 | 6/2015 | Tsoukalis |
| 2015/0379237 A1 | 12/2015 | Mills et al. |
| 2016/0015885 A1 | 1/2016 | Pananen et al. |
| 2016/0034655 A1 | 2/2016 | Gray et al. |
| 2016/0051749 A1 | 2/2016 | Istoc |
| 2016/0051751 A1 | 2/2016 | Silkaitis et al. |
| 2016/0103960 A1 | 4/2016 | Hume et al. |
| 2016/0228633 A1 | 8/2016 | Welsch et al. |
| 2016/0350513 A1 | 12/2016 | Jacobson et al. |
| 2017/0246388 A1 | 8/2017 | Kohlbrecher |
| 2017/0262590 A1 | 9/2017 | Karakosta et al. |
| 2017/0274140 A1 | 9/2017 | Howard et al. |
| 2017/0286637 A1 | 10/2017 | Arrizza et al. |
| 2017/0331735 A1 | 11/2017 | Jha et al. |
| 2018/0008772 A1 | 1/2018 | Wehba et al. |
| 2018/0028742 A1 | 2/2018 | Day et al. |

(56) References Cited

U.S. PATENT DOCUMENTS

| | | |
|---|---|---|
| 2018/0043094 A1 | 2/2018 | Day et al. |
| 2018/0121613 A1 | 5/2018 | Connely, IV et al. |
| 2018/0181712 A1 | 6/2018 | Ensey et al. |
| 2019/0096518 A1 | 3/2019 | Pace |
| 2019/0147998 A1 | 5/2019 | Ruchti et al. |
| 2019/0228863 A1 | 7/2019 | Dharwad et al. |
| 2019/0240405 A1 | 8/2019 | Wehba et al. |
| 2019/0243829 A1 | 8/2019 | Butler et al. |
| 2019/0269852 A1 | 9/2019 | Kohlbrecher |
| 2019/0311803 A1 | 10/2019 | Kohlbrecher et al. |

FOREIGN PATENT DOCUMENTS

| | | |
|---|---|---|
| CA | 2 898 825 | 7/2014 |
| CO | 01110843 | 8/2003 |
| DE | 31 12 762 | 1/1983 |
| DE | 34 35 647 | 7/1985 |
| DE | 198 44 252 | 3/2000 |
| DE | 199 32 147 | 1/2001 |
| DE | 103 52 456 | 7/2005 |
| EP | 0 319 267 | 6/1989 |
| EP | 0 380 061 | 8/1990 |
| EP | 0 384 155 | 8/1990 |
| EP | 0 460 533 | 12/1991 |
| EP | 0 564 127 | 6/1993 |
| EP | 0 633 035 | 1/1995 |
| EP | 0 652 528 | 5/1995 |
| EP | 0 672 427 | 9/1995 |
| EP | 0 683 465 | 11/1995 |
| EP | 0 880 936 | 12/1998 |
| EP | 1 157 711 | 11/2001 |
| EP | 1 174 817 | 1/2002 |
| EP | 0 664 102 | 4/2002 |
| EP | 1 197 178 | 4/2002 |
| EP | 0 830 775 | 8/2002 |
| EP | 1 500 025 | 4/2003 |
| EP | 2 113 842 | 11/2009 |
| EP | 2 228 004 | 9/2010 |
| EP | 2 243 506 | 10/2010 |
| EP | 2 410 448 | 1/2012 |
| EP | 2 742 961 | 6/2014 |
| FR | 2 717 919 | 9/1995 |
| GB | 2 285 135 | 6/1995 |
| JP | 04-161139 | 6/1992 |
| JP | H07-502678 | 3/1995 |
| JP | 11-500643 | 1/1999 |
| JP | 2000-316820 | 11/2000 |
| JP | 2002-531154 | 9/2002 |
| JP | 2003-016183 | 1/2003 |
| JP | 2003-296173 | 10/2003 |
| JP | 2005-021463 | 1/2005 |
| JP | 2005-527284 | 9/2005 |
| JP | 2005-284846 | 10/2005 |
| JP | 2006-047319 | 2/2006 |
| JP | 2006-520949 | 9/2006 |
| JP | 2007-518479 | 7/2007 |
| JP | 2008-080036 | 4/2008 |
| JP | 2008-516303 | 5/2008 |
| JP | 2008-158622 | 7/2008 |
| JP | 2008-529675 | 8/2008 |
| JP | 2009-163534 | 7/2009 |
| JP | 2010-502361 | 1/2010 |
| JP | 2012-070991 | 4/2012 |
| WO | WO 84/001719 | 5/1984 |
| WO | WO 91/016416 | 10/1991 |
| WO | WO 92/010985 | 7/1992 |
| WO | WO 92/013322 | 8/1992 |
| WO | WO 94/005355 | 3/1994 |
| WO | WO 96/008755 | 3/1996 |
| WO | WO 96/025186 | 8/1996 |
| WO | WO 98/012670 | 3/1998 |
| WO | WO 98/019263 | 5/1998 |
| WO | WO 99/051003 | 10/1999 |
| WO | WO 00/013580 | 3/2000 |
| WO | WO 00/053243 | 9/2000 |
| WO | WO 01/014974 | 3/2001 |
| WO | WO 01/033484 | 5/2001 |
| WO | WO 01/045014 | 6/2001 |
| WO | WO 02/005702 | 1/2002 |
| WO | WO 02/036044 | 5/2002 |
| WO | WO 02/049153 | 6/2002 |
| WO | WO 02/049279 | 6/2002 |
| WO | WO 02/069099 | 9/2002 |
| WO | WO 02/081015 | 10/2002 |
| WO | WO 02/088875 | 11/2002 |
| WO | WO 03/006091 | 1/2003 |
| WO | WO 03/050917 | 6/2003 |
| WO | WO 03/091836 | 11/2003 |
| WO | WO 03/094092 | 11/2003 |
| WO | WO 2004/060455 | 7/2004 |
| WO | WO 2004/070557 | 8/2004 |
| WO | WO 2004/070562 | 8/2004 |
| WO | WO 2004/072828 | 8/2004 |
| WO | WO 2005/036447 | 4/2005 |
| WO | WO 2005/057175 | 6/2005 |
| WO | WO 2005/066872 | 7/2005 |
| WO | WO 2007/087443 | 8/2007 |
| WO | WO 2007/117705 | 10/2007 |
| WO | WO 2007/127879 | 11/2007 |
| WO | WO 2007/127880 | 11/2007 |
| WO | WO 2008/067245 | 6/2008 |
| WO | WO 2008/082854 | 7/2008 |
| WO | WO 2008/088490 | 7/2008 |
| WO | WO 2008/097316 | 8/2008 |
| WO | WO 2008/103915 | 8/2008 |
| WO | WO 2008/124478 | 10/2008 |
| WO | WO 2008/134146 | 11/2008 |
| WO | WO 2009/016504 | 2/2009 |
| WO | WO 2009/023406 | 2/2009 |
| WO | WO 2009/023407 | 2/2009 |
| WO | WO 2009/023634 | 2/2009 |
| WO | WO 2009/036327 | 3/2009 |
| WO | WO 2009/049252 | 4/2009 |
| WO | WO 2010/017279 | 2/2010 |
| WO | WO 2010/033919 | 3/2010 |
| WO | WO 2010/053703 | 5/2010 |
| WO | WO 2010/075371 | 7/2010 |
| WO | WO 2010/099313 | 9/2010 |
| WO | WO 2010/114929 | 10/2010 |
| WO | WO 2010/119409 | 10/2010 |
| WO | WO 2010/124127 | 10/2010 |
| WO | WO 2010/130992 | 11/2010 |
| WO | WO 2010/135646 | 11/2010 |
| WO | WO 2010/135654 | 11/2010 |
| WO | WO 2010/135686 | 11/2010 |
| WO | WO 2011/005633 | 1/2011 |
| WO | WO 2011/022549 | 2/2011 |
| WO | WO 2012/048833 | 4/2012 |
| WO | WO 2012/049214 | 4/2012 |
| WO | WO 2012/049218 | 4/2012 |
| WO | WO 2012/120078 | 9/2012 |
| WO | WO 2012/140547 | 10/2012 |
| WO | WO 2012/164556 | 12/2012 |
| WO | WO 2012/170942 | 12/2012 |
| WO | WO 2013/045506 | 4/2013 |
| WO | WO 2014/100736 | 6/2014 |
| WO | WO 2014/131729 | 9/2014 |
| WO | WO 2014/131730 | 9/2014 |
| WO | WO 2015/124569 | 8/2015 |
| WO | WO 2017/176928 | 10/2017 |

OTHER PUBLICATIONS

Graseby, "Model 3000/500 and Micro 3100/505: Volumetric Infusion Pump", Technical Service Manual, Graseby Medical Ltd., Apr. 2002, Issue A, pp. 160.

Graseby, "Model 3000/500 and Micro 3100/505: Volumetric Infusion Pump: Illustrated Parts List for Pump Serial No. from 3000 to 59,999", Technical Service Manual, Graseby Medical Ltd., Apr. 2002, Issue A, pp. 71.

International Search Report and Written Opinion received in PCT Application No. PCT/US2014/056531, dated Jan. 14, 2015 in 9 pages.

(56) References Cited

OTHER PUBLICATIONS

Micrel Medical Devices, "MP Daily +" http://web.archive.org/web/20130803235715/http://www.micrelmed.com/index.aspx?productid=9 as archived Aug. 3, 2013 in 1 page.
Passos et al., "Distributed Software Platform for Automation and Control of General Anaesthesia", Eighth International Symposium on Parallel and Distributed Computing, ISPDC '09, Jun. 30-Jul. 4, 2009, pp. 8.
Gabel et al., "Camp: A Common API for Measuring Performance", 21st Large Installations System Administration Conference (LISA '07), 2007, pp. 49-61.
Akridge, Jeannie, "New Pumps Outsmart User Error" Healthcare Purchasing News, Apr. 2011, pp. 10, http://web.archive.org/web/20110426122450/http://www.hponline.com/inside/2011-01/1104-OR-Pumps.html.
Alur et al., "Formal Specifications and Analysis of the Computer-Assisted Resuscitation Algorithm (CARA) Infusion Pump Control System", International Journal on Software Tools for Technology Transfer, Feb. 2004, vol. 5, No. 4, pp. 308-319.
Aragon, Daleen RN, Ph.D., CCRN, "Evaluation of Nursing Work Effort and Perceptions About Blood Glucose Testing in Tight Glycemic Control", American Journal of Critical Care, Jul. 2006, vol. 15, No. 4, pp. 370-377.
ASHP Advantage, "Improving Medication Safety in Health Systems Through Innovations in Automation Technology", Proceedings of Educational Symposium and Educational Sessions during the 39th ASHP Midyear Clinical Meeting, Dec. 5-9, 2004, Orlando, FL, pp. 28.
Beard et al., "Total Quality Pain Management: History, Background, Resources", Abbott Laboratories, TQPM Survey History, available Feb. 2015 or earlier, pp. 1-3.
Bektas et al., "Bluetooth Communication Employing Antenna Diversity", Proceedings of Eight IEEE International Symposium on Computers and Communication, Jul. 2003, pp. 6.
Bequette, Ph.D., "A Critical Assessment of Algorithms and Challenges in the Development of a Closed-Loop Artificial Pancreas", Diabetes Technology & Therapeutics, Feb. 28, 2005, vol. 7, No. 1, pp. 28-47.
Bequette, B. Wayne, Ph.D., "Analysis of Algorithms for Intensive Care Unit Blood Glucose Control", Journal of Diabetes Science and Technology, Nov. 2007, vol. 1, No. 6, pp. 813-824.
Braun, "Infusomat® Space and Accessories", Instructions for Use, Nov. 2010, pp. 68. http://corp.bbraun/ee/Extranet/Infusiononipumbad/Kasutusjuhendid/Vanad/Kasutusijuhend-infusomat_Space(vers688J.Inglise_k).pdf.
Brownlee, Seth, "Product Spotlight: The Plum A+ with Hospira MedNet Infusion System", PP&P Magazine, Dec. 2005, vol. 2, No. 7, pp. 2.
Cannon, MD et al., "Automated Heparin-Delivery System to Control Activated Partial Thromboplastin Time", Circulation, Feb. 16, 1999, vol. 99, pp. 751-756.
"CareAware® Infusion Management", Cerner Store, as printed May 12, 2011, pp. 3, https://store.cerner.com/items/7.
Chen et al., "Enabling Location-Based Services on Wireless LANs", The 11th IEEE International Conference on Networks, ICON 2003, Sep. 28-Oct. 1, 2003, pp. 567-572.
"Computer Dictionary", Microsoft Press, Third Edition, Microsoft Press, 1997, pp. 430 & 506.
Crawford, Anne J., MSN, RNC, "Building a Successful Quality Pain Service: Using Patient Satisfaction Data and the Clinical Practice Guideline", USA, 1995, pp. 1-6.
Crocker et al., "Augmented BNF for Syntax Specifications: ABNF", Network Working Group, Standards Track, Jan. 2008, pp. 16.
Davidson et al., "A Computer-Directed Intravenous Insulin System Shown to be Safe, Simple, and Effective in 120,618 h of Operation", Diabetes Care, Oct. 2005, vol. 28, No. 10, pp. 2418-2423.
Davies, T., "Cordless Data Acquisition in a Hospital Environment", IEE Colloquium on Cordless Computing—Systems and User Experience, 1993, pp. 4.

Dayhoff et al., "Medical Data Capture and Display: The Importance of Clinicians' Workstation Design", AMIA, Inc., 1994, pp. 541-545.
Diabetes Close Up, Close Concerns AACE Inpatient Management Conference Report, Consensus Development Conference on Inpatient Diabetes and Metabolic Control, Washington, D.C., Dec. 14-16, 2003, pp. 1-32.
East PhD et al., "Digital Electronic Communication Between ICU Ventilators and Computers and Printers", Respiratory Care, Sep. 1992, vol. 37, No. 9, pp. 1113-1122.
Einhorn, George W., "Total Quality Pain Management: A Computerized Quality Assessment Tool for Postoperative Pain Management", Abbott Laboratories, Chicago, IL, Mar. 2, 2000, pp. 1-4.
Eskew et al., "Using Innovative Technologies to Set New Safety Standards for the Infusion of Intravenous Medications", Hospital Pharmacy, 2002, vol. 37, No. 11, pp. 1179-1189.
Philips, "IntelliSpace Event Management and IntelliVue Patient Monitoring", Release 10, 2011, http://incenter.medical.phillips.com/docllb/enc/fetch/2000/4504/577242/577243/577247/582646/583147/8359175/Phillips_Monitoring_and_IntelliSpace_Event_Management_Interoperabillity.pdf%3fnodeid%3d8508574%226vernum%3d-2, pp. 2.
Felleiter et al., "Data Processing in Prehospital Emergency Medicine", International journal of Clinical Monitoring and Computing, Feb. 1995, vol. 12, No. 1, pp. 37-41.
Fogt et al., Development and Evaluation of a Glucose Analyzer for a Glucose-Controlled Insulin Infusion System (Biostator®), Clinical Chemistry, 1978, vol. 24, No. 8, pp. 1366-1372.
Gage et al., "Automated Anesthesia Surgery Medical Record System", International Journal of Clinical Monitoring and Computing, Dec. 1990, vol. 7, No. 4, pp. 259-263.
Galt et al., "Personal Digital Assistant-Based Drug Information Sources: Potential to Improve Medication Safety", Journal of Medical Library Association, Apr. 2005, vol. 93, No. 2, pp. 229-236.
Gardner, Ph.D. et al., "Real Time Data Acquisition: Recommendations for the Medical Information Bus (MIB)", 1992, pp. 813-817.
"General-Purpose Infusion Pumps", Health Devices, EXRI Institute, Oct. 1, 2002, vol. 31, No. 10, pp. 353-387.
Givens et al., "Exploring the Internal State of User Interfaces by Combining Computer Vision Techniques with Grammatical Inference", Proceedings of the 2013 International Conference on Software Engineering, San Francisco, CA, May 18-26, 2013, pp. 1165-1168.
Glaeser, "A Hierarchical Minicomputer System for Continuous Post-Surgical Monitoring", Computers and Biomedical Research, Aug. 31, 1975, pp. 336-361.
Goldberg et al., "Clinical Results of an Updated Insulin Infusion Protocol in Critically Ill Patients", Diabetes Spectrum, 2005, vol. 18, No. 3, pp. 188-191.
Gomez et al., "CLAM: Connection-Less, Lightweight, and Multiway Communication Support for Distributed Computing", Computer Science, 1997, vol. 1199, pp. 227-240.
"GPS Tracker for Medical Equipment", http://www.trackingsystem.com/forbusiness/corporate-trackingsystems/1098-gps-tracker-formedicalequipment.html, Mar. 15, 2015, pp. 2.
Halpern et al., "Changes in Critical Care Beds and Occupancy in the United States 1985-2000: Differences Attributable to Hospital Size", Critical Care Medical, Aug. 2006, vol. 34, No. 8, pp. 2105-2112.
Hamann et al., "PUMPSIM: A Software Package for Simulating Computer-Controlled Drug Infusion Pumps", Annual International Conference of the IEEE Engineering in Medicine and Biology Society, 1990, vol. 12, No. 5, pp. 2019-2020.
Hasegawa et al., "On a Portable Memory Device for Physical Activities and Informations of Maternal Perception", Journal of Perinatal Medicine, 1988, vol. 16, No. 4, pp. 349-356.
Hawley et al., "Clinical Implementation of an Automated Medical Information Bus in an Intensive Care Unit", Proceedings of the Annual Symposium on Computer Application in Medical Care, Nov. 9, 1988, pp. 621-624.
Hayes-Roth et al., "Guardian: A Prototype Intelligent Agent for Intensive-Care Monitoring", Artificial Intelligence in Medicine, vol. 4, Dec. 31, 1992, pp. 165-185.

(56) References Cited

OTHER PUBLICATIONS

Hospira, Gemstar® Pain Management Infusion System 9-084-PR1-2-2, www.hospira.com/prodcuts.gemstar_painmanagement.aspx, Jan. 28, 2010, pp. 1-2.
Introducing Abbott TQPM (Total Quality Pain Management), Abbott Laboratories, Abbott Park, IL, May 2000, pp. 1-4.
"Infusion Pump", Wikipedia.org, https://web.archive.org/web/20140703024932/https://en.wikipedia.org/wiki/Infusion_pump, as last modified Mar. 27, 2014, pp. 3.
Isaka et al., "Control Strategies for Arterial Blood Pressure Regulation", IEEE Transactions on Biomedical Engineering, Apr. 1993, vol. 40, No. 4, pp. 353-363.
Johnson et al., "Using Bcma Software to Improve Patient Safety in Veterans Administration Medical Centers", Journal of Healthcare Information Management, Dec. 6, 2004, vol. 16, No. 1, pp. 46-51.
Kent Displays, "Reflex ™ Electronic Skins", Product Brief 25127B, 2009, pp. 2.
Kent Displays, "Reflex Electronic Skins Engineering Evaluation Kit", 25136A, Mar. 10, 2009.
Lefkowitz et al., "A Trial of the Use of Bar Code Technology to Restructure a Drug Distribution and Administration System", Hospital Pharmacy, Mar. 31, 1991, vol. 26, No. 3, pp. 239-242.
Lenssen et al., "Bright Color Electronic Paper Technology and Applications", IDS '09 Publication EP1-2 (Phillips Research), 2009, pp. 529-532.
Leveson, Nancy, "Medical Devices: The Therac-25", Appendix A, University of Washington, 1995, pp. 49.
Linkens, D.A. "Computer Control for Patient Care", Computer Control of Real-Time Processes, IEE Control Engineering Series 41, 1990, Ch. 13, pp. 216-238.
Mako Hill et al., "The Official Ubuntu Book", Shoeisha Co., Ltd., 1st Edition, Jun. 11, 2007, pp. 115 to 125.
Marshall, et al., "New Microprocessor-Based Insulin Controller", IEEE Transactions on Biomedical Engineering, Nov. 1983, vol. BME-30, No. 11, pp. 689-695.
Martino et al., "Automation of a Medical Intensive Care Environment with a Flexible Configuration of Computer Systems", Proceedings of the Annual Symposium on Computer Application in Medical Care, Nov. 5, 1980, vol. 3, pp. 1562-1568.
Matsunaga et al., "On the Use of Machine Learning to Predict the Time and Resources Consumed by Applications", 2010 10th IEEE/ACM International Conference on Cluster, Cloud and Grid Computing (CCGrid), May 17-20, 2010, pp. 495-504.
Mauseth et al., "Proposed Clinical Application for Tuning Fuzzy Logic Controller of Artificial Pancreas Utilizing a Personalization Factor", Journal of Diabetes Science and Technology, Jul. 2010, vol. 4, No. 4, pp. 913-922.
Medfusion™, "Medfusion Syringe Infusion Pump Model 4000", Operator's Manual, Software Version V1.1, Sep. 2011, pp. 154. http://www.medfusionpump.com/assets/literature/manuals/Operators_Manual_4000_40-5760-51A.pdf.
Metnitz et al., "Computer Assisted Data Analysis in Intensive Care: the ICDEV Project-Development of a Scientific Database System for Intensive Care", International Journal of Clinical Monitoring and Computing, Aug. 1995, vol. 12, No. 3, pp. 147-159.
Moghissi, Etie, MD, FACP, FACE, "Hyperglycemia in Hospitalized Patients", A Supplement to ACP Hospitalist, Jun. 15, 2008, pp. 32.
Murray, Jr. et al., "Automated Drug Identification System (during surgery)", IEEE Proceedings of Southeastcon '91, Apr. 7-10, 1991, pp. 265.
Nicholson et al., "'Smart' Infusion Apparatus for Computation and Automated Delivery of Loading, Tapering, and Maintenance Infusion Regimens of Lidocaine, Procainamide, and Theophylline", Proceedings of The Seventh Annual Symposium on Computer Applications in Medical Care, Oct. 1983, pp. 212-213.
Nolan et al., "The P1073 Medical Information Bus Standard: Overview and Benefits for Clinical Users", 1990, pp. 216-219.
Omnilink Systems, Inc., "Portable Medical Equipment Tracking", http://www.omnilink.com/portablemedicalequipmenttracking/, Mar. 15, 2015, pp. 2.

O'Shea, Kristen L., "Infusion Management: Working Smarter, Not Harder", Hospital Pharmacy, Apr. 2013, vol. 48, No. 3, pp. S1-S14.
Package Management in Debian GNU/Linux, Debian GNU/Linux Expert Desktop Use Special, Giutsu-Hyohron Co., Ltd., First Edition, Sep. 25, 2004, pp. 183-185.
Pretty et al., "Hypoglycemia Detection in Critical Care Using Continuous Glucose Monitors: An in Silico Proof of Concept Analysis", Journal of Diabetes Science and Technology, Jan. 2010, vol. 4, No. 1, pp. 15-24.
Rappoport, Arthur E., "A Hospital Patient and Laboratory machine-Readable Identification System (MRIS) Revisited", Journal of Medical Systems, Apr. 1984, vol. 8, Nos. 1/2, pp. 133-156.
Ritchie et al., "A Microcomputer Based Controller for Neuromuscular Block During Surgery", Annals of Biomedical Engineering, Jan. 1985, vol. 13, No. 1, pp. 3-15.
Saager et al., "Computer-Guided Versus Standard Protocol for Insulin Administration in Diabetic Patients Undergoing Cardiac Surgery", Annual Meeting of the American Society of Critical Care Anesthesiologists, Oct. 13, 2006.
Sanders et al., "The Computer in a Programmable Implantable Medication System (PIMS)", Proceedings of the Annual Symposium on Computer Application in Medical Care, Nov. 2, 1982, pp. 682-685.
Schilling et al., "Optimizing Outcomes! Error Prevention and Evidence-Based Practice with IV Medications", A Pro-Ce Publication, Hospira, Inc., Feb. 6, 2012, pp. 56.
Schulze et al., "Advanced Sensors Technology Survey", Final Report, Feb. 10, 1992, pp. 161.
Scott, et al., "Using Bar-Code Technology to Capture Clinical Intervention Data in a Hospital with a Stand-Alone Pharmacy Computer System", Mar. 15, 1996, American Journal of Health-System Pharmacy, vol. 53, No. 6, pp. 651-654.
Sebald et al., "Numerical Analysis of a Comprehensive in Silico Subcutaneous Insulin Absorption Compartmental Model", 31st Annual International Conference of the IEEE Engineering in Medicine and Biology Society, Sep. 2-6, 2009, pp. 3901-3904.
Shabot, M. Michael, "Standardized Acquisition of Bedside Data: The IEEE P1073 Medical Information Bus", International Journal of Clinical Monitoring and Computing, vol. 6, Sep. 27, 1989, pp. 197-204.
Sheppard, Louis, Ph.D., "Automation of the Infusion of Drugs Using Feedback Control", Journal of Cardiothoracic and Vascular Anesthesia, Feb. 28, 1989, vol. 3, No. 1, pp. 1-3.
Sheppard, Louis, Ph D., "Computer Control of the Infusion of Vasocactive Drugs", Annals of Biomedical Engineering, Jul. 1980, vol. 8, No. 4-6, pp. 431-444.
Sheppard, Louis, Ph.D., "The Application of Computers to the Measurement, Analysis, and Treatment of Patients Following Cardiac Surgical Procedures", The University of Alabama in Birmingham, Oct. 31, 1977, pp. 297-300.
Sheppard, Louis, Ph.D., "The Computer in the Care of Critically Ill Patients", Proceedings of the IEEE, Sep. 1979, vol. 67, No. 9, pp. 1300-1306.
"Sigma Spectrum: Operator's Manual", Oct. 2009, pp. 72. http://static.medonecapital.com/manuals/userManuals/Sigma-Spectrum-Operator-Manual-October-2009.pdf.
Simonsen, Michael Ph.D., POC Testing, New Monitoring Strategies on Fast Growth Paths in European Healthcare Arenas, Biomedical Business & Technology, Jan. 2007, vol. 30, No. 1, pp. 1-36.
Siv-Lee et al., "Implementation of Wireless 'Intelligent' Pump IV Infusion Technology in a Not-for-Profit Academic Hospital Setting", Hospital Pharmacy, Sep. 2007, vol. 42, No. 9, pp. 832-840. http://www.thomasland.com/hpl4209-832.pdf.
Slack, W.V. "Information Technologies for Transforming Health Care", https://www.andrew.cmu.edu/course/90-853/medis.dir/03ch2.pdf, Ch. 2, 1995, pp. 29-78.
Smith, Joe, "Infusion Pump Informatics", CatalyzeCare: Transforming Healthcare, as printed May 12, 2011, pp. 2.
Sodder, Lisa, "A Center Keeps Medicine in Right Hands", Dec. 4, 1999, pp. 1-2.

(56) References Cited

OTHER PUBLICATIONS

Stitt, F.W., "The Problem-Oriented Medical Synopsis: a Patient-Centered Clinical Information System", Proceedings of the Annual Symposium on Computer Application in Medical Care, 1994, pp. 88-92.
Stokowski, Laura A. RN, MS, "Using Technology to Improve Medication Safety in the Newborn Intensive Care Unit", Advances in Neonatal Care, Dec. 2001, vol. 1, No. 2, pp. 70-83.
Sutton et al., "The Syntax and Semantics of the PROforma Guideline Modeling Language", Journal of the American Medical Informatics Association, Sep./Oct. 2003, vol. 10, No. 5, pp. 433-443.
Szeinbach et al., "Automated Dispensing Technologies: Effect on Managed Care", Journal of Managed Care Pharmacy (JMCP), Sep./Oct. 1995, vol. 1, No. 2, pp. 121-127.
Szolovits et al., "Guardian Angel: Patient-Centered Health Information Systems", Technical Report MIT/LCS/TR-604, Massachusetts Institute of Technology Laboratory for Computer Science, May 1994, pp. 39.
Van Den Berghe, M.D., Ph.D., et al., "Intensive Insulin Therapy in Critically Ill Patients", The New England Journal of Medicine, Nov. 8, 2001, vol. 345, No. 19, pp. 1359-1367.
Van Den Berghe, M.D., Ph.D., et al., "Intensive Insulin Therapy in the Medical ICU", The New England Journal of Medicine, Feb. 2, 2006, vol. 354, No. 5, pp. 449-461.
Van Der Maas et al., "Requirements for Medical Modeling Languages", Journal of the American Medical Informatics Association, Mar./Apr. 2001, vol. 8, No. 2, pp. 146-162.
Villalobos et al., "Computerized System in Intensive Care medicine", Medical Informatics, vol. 11, No. 3, 1986, pp. 269-275.
Wilkins et al., "A Regular Language: The Annotated Case Report Form", PPD Inc., PharmaSUG2011—Paper CD18, 2011, pp. 1-9.
Ying et al., "Regulating Mean Arterial Pressure in Postsurgical Cardiac Patients. A Fuzzy Logic System to Control Administration of Sodium Nitroprusside", IEEE Engineering in Medicine and Biology Magazine, vol. 13, No. 5, Nov.-Dec. 1994, pp. 671-677.
Yue, Ying Kwan, "A Healthcare Failure Mode and Effect Analysis on the Safety of Secondary Infusions", Thesis, Institute of Biomaterials and Biomedical Engineering, University of Toronto, 2012, pp. 168.
Yurkonis et al., "Computer Simulation of Adaptive Drug Infusion", IEEE Transactions on Biomedical Engineering, vol. BME-34, No. 8, Aug. 1987, pp. 633-635.
Zakariah et al., "Combination of Biphasic Transmittance Waveform with Blood Procalcitonin Levels for Diagnosis of Sepsis in Acutely Ill Patients", Critical Care Medicine, 2008, vol. 36, No. 5, pp. 1507-1512.
"File Verification", Wikipedia.org, dated Oct. 11, 2011 in 2 pages, https://en.wikipedia.org/w/index.php?title=File_verification&oldid=455048290.
"Software Versioning", Wikipedia.org, dated Oct. 16, 2011 in 11 pages, https://en.wikipedia/org/w/index.pdp=title=Software_versioning&oldid=455859110.

\* cited by examiner

| Cephalosporin | | |
|---|---|---|
| | 1 g / 100 mL | Controlled restart in progress |
| Dose | | |
| | 1000 mg/hr | |
| Rate | | |
| | 100 mL/hr |  |
| VTBI | | |
| | 275 mL | |

| Cephalosporin | | |
|---|---|---|
| | 1 g / 100 mL | Reboot Unsuccessful. Pump Stops In 4 min 23 sec |
| Dose | | |
| | 1000 mg/hr | |
| Rate | | |
| | 100 mL/hr | |
| VTBI | |  |
| | 275 mL | |

FAIL-SAFE DRUG INFUSION THERAPY SYSTEM

REFERENCE TO RELATED APPLICATIONS

This application is a continuation of U.S. patent application Ser. No. 14/490,450, filed Sep. 18, 2014, titled "Fail-Safe Drug Infusion Therapy System," which claims the benefit of the filing date and priority of U.S. Provisional Application No. 61/880,656, filed Sep. 20, 2013, titled "Fail-Safe Drug Infusion Therapy System," the entire contents of each are hereby incorporated by reference herein and made part of this specification for all that they disclose.

BACKGROUND OF THE INVENTION

Field of the Invention

One or more embodiments of the invention are related to drug infusion therapy systems. More particularly, but not by way of limitation, one or more embodiments of the invention enable a fail-safe drug infusion system, including a user interface controller (UIC) and at least one pump motor controller (PMC), with protocols that enable the PMC to operate therapy delivery for a limited amount of time in the event that UIC fails or the communication link between the UIC and the PMC is interrupted. Embodiments also include synchronization methods to synchronize the delivered drug status back to the UIC after the UIC reboots or after the communication link between the UIC and the PMC is restored. The PMC may apply intelligent fail-safe drug infusion therapy by temporarily displaying therapy information, for example information normally displayed on the UIC, while taking control of alarm signaling and providing minimal user control of the therapy until the UIC restores itself, the infusion completes normally, or the user stops the infusion. If the PMC becomes inoperable, the UIC may wait for the PMC to reboot, or attempt to switch drug infusion channels to provide robust drug infusion.

Description of the Related Art

Generally, current drug infusion systems do not synchronize information between multiple processors, or controllers, in order to enable one processor, or controller, to take over in a failsafe mode and eventually recover from errors in the other processor or after restoring communications between processors. Some known systems utilize a secondary processor known as a "Safety Processor", wherein such a safety processor may be used to keep the apparatus powered and to ensure delivery of a drug. These locally redundant systems generally switch to a redundant processor that may contain complex business logic inherent in the first processor, i.e., in the user interface code, which limits the robustness of the system since an error on the first processor may also occur on a second processor having the same or similar complex software code. In the event of a fault detected by either processor, including failure or loss of communication with the primary processor, the infusion may be stopped. Absent prompt caregiver attention and intervention, stopping some drug infusions may result in a delay in therapy that could lead to serious injury to a patient or even death.

In addition, current distributed systems appear to lack any suggestion of using a user interface controller (UIC), and a pump motor controller (PMC), that both maintain redundant, yet separate ability to manage alarm signals, user inputs, user displays, etc., to ensure continuous delivery of drugs in a robust manner. For example, typical systems lack any disclosure of limited backup capability in a microcontroller in the PMC, for example do not display infusion status on the PMC display that would normally be displayed on the UIC. Hence, these systems cannot possibly maintain fail-safe operation since no backup functionality exists for displaying infusion status, alarms or signals.

For example, U.S. Pat. No. 7,835,927 to Coffman et al., entitled "Medication Management System", discloses a medical database carrier that may communicate information regarding medication delivery and other patient information between a control system in communication with a care-giving facility. As such, the system appears to lack any disclosure of fail-safe operation if a communication link between a first processor and a second processor is lost. For example, the system does not contemplate replacing the second processor's duties for the current delivery process, to continue to deliver a drug or medication, and to continue to power the system. The system also lacks any disclosure or suggestion of synchronizing delivery status after the communication link has been restored.

United States Patent Publication 20100200506 to Boehnlein et al., entitled "Flow Balancing and Synchronization System and Method, Especially for Citrate", appears to disclose a renal failure therapy system including a blood pump, a citrate pump and a control unit configured to automatically control the blood pump and the citrate pump, for synchronization of flow rates. The system of Boehnlein et al., for example, discloses automatically adjusting for variations in flow rate, if one pump increases or decreases flow rate, using an external pump. In addition, the system appears to disclose a control processor in communication with a safety processor and two pumps, to monitor error conditions, receive status and parameter information from each of the pumps, ensuring safety limits are met. For example, if one pump is only inputting less ml/hour, an alarm is generated and the system automatically compensates for the loss by varying the pump rate of another pump. However, it appears as though the system lacks any disclosure of fail-safe operation if a communication link between a first processor and a second processor is lost. For example, the system does not contemplate replacing the second processor's duties for the current delivery process, to continue to deliver a drug or medication, and to continue to power the system. The system also lacks any disclosure or suggestion of synchronizing delivery statuses after the communication link has been restored.

In summary, there are no known fail-safe drug infusion therapy systems, including a first processor and a second processor, with protocols that enable the second processor to operate therapy delivery for a limited amount of time in the event that the communication link between the first processor and the second processor is interrupted that include synchronization methods to synchronize the second processor and the delivered drug status back to the first processor. In addition, there are no known fail-safe drug infusion therapy systems that display infusion progress and infusion statuses for example on a limited display connected to the PMC when the UIC is inoperable or when communication link is interrupted. For at least the limitations described above there is a need for a drug infusion system for synchronized fail-safe drug infusion therapy.

SUMMARY OF THE INVENTION

One or more embodiments described in the specification are related to drug infusion therapy systems that provide synchronized fail-safe drug infusion therapy. In one or more embodiments, the drug infusion system includes distributed components that include a user interface controller (UIC) generally having complex business logic and complex user interface functionality, and at least one pump motor controller (PMC) acting as a real-time controller, wherein the UIC and PMC communicate over a communication link.

According to at least one embodiment, the UIC includes a first processor, a first memory coupled with the first processor and a user interface display coupled with the first processor. In at least one embodiment, the PMC includes a second processor, a second memory coupled with the second processor and a pump motor controller display coupled with the second processor. The second processor, in at least one embodiment, controls a pump motor to deliver a fluid, for example one or more drugs. The pump motor controller display may have limited capabilities and be utilized as a backup display if the UIC cannot display infusion status. In one or more embodiments, the first processor and the second processor are communicatively synchronized via the communication link.

Embodiments of the invention may be also redundant on a local component level as well. For example, in one or more embodiments, the UIC can "move" a running infusion to another unused channel. For example, in a dual channel system configuration, if one channel fails while executing a program, the UIC can prompt the user to move the administration set, which may include a cassette, over to the other channel and resume the infusion from there. Thus embodiments, of the invention may include robust distributed and local components.

By way of one or more embodiments, the UIC may build a "token" that contains the drug infusion program as confirmed by the user along with the current infusion status. Specifically, the "token" or drug infusion program may include all program steps, all infusion related options and current status, which is initially null before infusion begins in one or more embodiments. The token may act in one or more embodiments as a semaphore for the component that has the responsibility to maintain the current infusion status for example.

The UIC may pass the token to the PMC to initiate drug infusion. The PMC then runs the infusion therapy and monitors communication with the UIC. While running the program, the PMC updates the UIC with an infusion status update message. The message may contain the currently executing program and associated program steps, the infusion related options and current status, e.g., the most up to date information about the delivered and remaining to be delivered infusion parameters. Under normal processing, the status details are synchronized with the UIC over time, for example at predefined time intervals.

If the UIC fails, for example via failure to provide heartbeat to the PMC, the PMC takes control of the alarm components and signals the failure to the user, albeit on a limited display local to the PMC for example or alternatively using operable portions of the UIC related display. During this time, the PMC may display infusion progress and status locally, for example replacing the current limited text or graphics display with infusion related information that would normally be displayed on the UIC. Alternatively, if any components normally controlled by the UIC, such as the display are still operative, then the PMC may pass the information to the display of the UIC or a display common to both the UIC and PMC. The PMC may also raise audio and visual alarms locally or remotely until the UIC is functional, which is generally the responsibility of the UIC when functional. In one or more embodiments, the display or backup display of the PMC may show the amount of time that the PMC may operate independently based on the current drug infusion program for example. When another infusion related event occurs, such as an occlusion, or air-in-line, etc., the PMC takes intelligent local actions based on the initial program received to handle the condition, for example stop or not stop infusion accordingly along with signaling of the new alarm condition. When any of the alarm conditions are cleared, including if the UIC recovers and reestablishes communication with the PMC, the system uses normal alarm condition clearing protocols.

If the PMC fails, for example via failure to provide heartbeat to the UIC, then the UIC may assert control of the token with the last known infusion parameters until the PMC reboots. The UIC may then pass the token back to the PMC with the last known infusion related information.

In one or more embodiments, each of the first memory of the first processor and the second memory of the second processor may include any type of redundant drug infusion data structures, for example queues, lists, databases or any other type of data structure. Queues such as service queues may be utilized to store delivery requests and queues such as redundant drug infusion working queues may be utilized to store in-progress infusion requests respectively. Any other data structures or techniques may be utilized to ensure synchronization of drug infusion information in keeping with the scope of the invention.

BRIEF DESCRIPTION OF THE DRAWINGS

The above and other aspects, features and advantages of the invention will be more apparent from the following more particular description thereof, presented in conjunction with the following drawings wherein.

DETAILED DESCRIPTION OF THE PREFERRED EMBODIMENT

A fail-safe drug infusion system will now be described. In the following exemplary description numerous specific details are set forth in order to provide a more thorough understanding of embodiments of the invention. It will be apparent, however, to an artisan of ordinary skill that the present invention may be practiced without incorporating all aspects of the specific details described herein. In other instances, specific features, quantities, or measurements well known to those of ordinary skill in the art have not been described in detail so as not to obscure the invention. Readers should note that although examples of the invention are set forth herein, the claims, and the full scope of any equivalents, are what define the metes and bounds of the invention.

Figure 1:
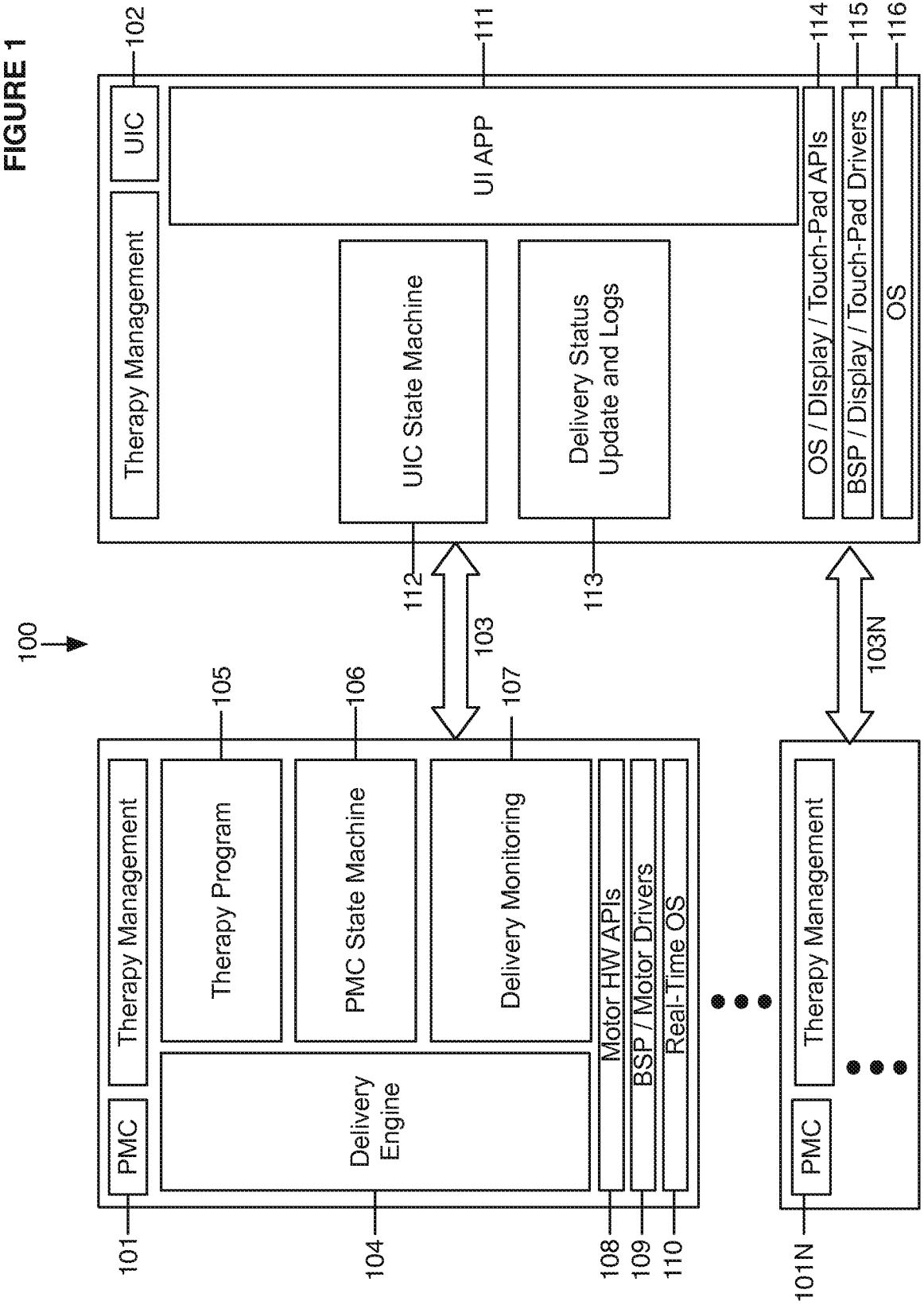
FIG. 1 shows a logical diagram of the fail-safe drug infusion therapy system according to one or more embodiments of the invention.

FIG. 1 shows a schematic overall diagram of the fail-safe drug infusion therapy system according to one or more embodiments of the invention. As shown in FIG. 1, by way of one or more embodiments, each of the first memory, that holds user interface app 111, user interface controller state machine 112, delivery status update and logs 113, operating system, display and touch-pad APIs 114, board support package, display and touch-pad drivers 115 and operating system 116 of the first processor 102 and the second memory, that holds delivery engine 104, therapy program 105, PMC state machine 106, delivery monitoring information 107, motor hardware APIs 108, board support package, motor drivers 109 and real-time operating system 110 of the second processor 101 include redundant drug infusion related information and status. The redundant drug infusion related information may be stored in the delivery monitoring 107 and delivery status 113 memory areas for example or in any other portion of memory in either the PMC or UIC. In one or more embodiments UIC 102 may control more than one PMC, e.g., PMC 101 and 101N.

In at least one or more embodiments of the invention, when the communication link is initially established between the first processor and the second processor, the first processor in the PMC obtains an infusion program and is initially responsible for maintaining infusion related information. In one or more embodiments this is accomplished with a "token" that contains the drug infusion program as confirmed by the user along with the current infusion status. Specifically, the "token" or drug infusion program may include all program steps, all infusion related options and current status, which is initially null before infusion begins in one or more embodiments. The token may act in one or more embodiments as a semaphore for the component that has the responsibility to maintain the current infusion status for example. According to at least one embodiment, the first processor may send a first delivery request from the first processor drug infusion service queue to the first processor drug infusion working queue. When the first delivery request is in the first processor drug infusion working queue, the first processor, when in active mode, may send a delivery request notification to the second processor via a first delivery request identification code. Any other type of data structure, messages or communication protocols that enable the PMC and UIC to maintain and synchronize infusion data after either processor malfunctions and/or enable the PMC to display infusion related information that is normally displayed on the UIC if the UIC malfunctions is in keeping with the scope of the invention.

In at least one or more embodiments, when the second processor receives the delivery request identification code, the second processor may transfer the first delivery request from the second processor drug infusion service queue to the second processor drug infusion working queue, and may command the pump motor to deliver the fluid. According to at least one embodiment of the invention, if the first processor fails or if the communication link between the first processor and the second processor is interrupted, the second processor may apply fail-safe therapy and shift from the slave mode to the master mode in order to process the second processor drug infusion service queue and drug infusion working queue to command the pump motor to deliver the fluid.

By way of one or more embodiments of the invention, when the pump motor delivers the fluid, the second processor creates a status report with status report information, such that the second processor may send the status report information to the first processor. In at least one embodiment, the first processor receives the status report information from the second processor and updates a fluid delivery status display on the user interface display 202 (see FIG. 2). According to one or more embodiments of the invention, the information includes the activated delivery requests, the activated fluid deliveries, completed delivery requests, completed fluid deliveries, and an ordered list of the delivery requests remaining in the first processor drug infusion service queue.

In one or more embodiments of the invention, the first processor may send a first delivery suspend request to the second processor in order to suspend the first delivery request, such as when the user initiates a first delivery suspend command, when the first processor detects an error, when the second processor detects an error, or any combination thereof. According to at least one embodiment, the second processor may receive the first delivery suspend request, stop the pump motor delivery of the fluid prior to completion of the delivery of the fluid such that undelivered fluid volume remains, and suspend the first delivery request in the second processor drug infusion working queue.

In at least one or more embodiments of the invention, the error detected by the first processor and/or the error detected by the second processor may include one or more of a UIC 102 failure, wherein infusion is continued while the UIC 102 reboots, motor encoder position error, wherein the motor encoder may attempt to recalibrate itself and pumping is continued instead of alarming and/or stopping infusion, low battery capacity, low battery voltage, indication of a lack of an installed battery, high battery charging current, a stuck button wherein the button is not the emergency stop button 201, a buzzer and/or speaker failure during infusion, a drug library download failure, wherein the UIC 102 may include or may access a drug library and during such a failure the UIC 102 may revert back to a previously installed drug library PIDL or a default drug library DDL. In one or more embodiments, the errors may include failure of the UIC 102 to write to log, a volume overshoot, lost communication with one or more external drug libraries, high ambient temperature or temperature sensor failure, and no heartbeat and/or communications between the UIC 102 and the PMC 101.

In one or more embodiments of the invention, the first processor may send a second delivery request from the first processor service queue to the first processor drug infusion working queue. As such, in at least one embodiment, when the second delivery request is in the first processor drug infusion working queue, the first processor may send a second delivery request notification to the second processor via a second delivery request identification code, and when the second processor receives the second delivery request identification code, the second processor may transfer the second delivery request from the second processor service queue to the second processor drug infusion working queue, such that the pump motor delivers the fluid.

In at least one embodiment of the invention, for piggyback requests for example, when the second delivery request fluid delivery is completed, the second processor may update the fluid delivery status display, and the first processor may send the suspended first delivery request to the second processor such that the pump motor delivers the remaining undelivered fluid volume.

By way of one or more embodiments, if the communication link 103, or 103N when communicating with more than one PMCs, between the first processor and the second processor is interrupted during fluid delivery of the second delivery request, upon completion of the second delivery request, the second processor may locate the suspended first delivery request from the second processor service queue and may transfer the suspended first delivery request to the second processor drug infusion working queue in order to deliver the remaining undelivered fluid volume. In at least one embodiment of the invention, when the remaining undelivered fluid volume is delivered, the first processor may locate a next delivery request from the delivery requests in the first processor service queue, such that the pump motor delivers the fluid. In one or more embodiments, when the remaining undelivered fluid volume is delivered, the second processor may locate a next delivery request from the delivery requests in the second processor service queue, such that the pump motor delivers the fluid.

In at least one embodiment, when the communication link 103 between the first processor and the second processor is interrupted, the second processor may provide therapy for a predefined time in active mode, or display information on the pump motor controller display or any combination thereof. The information may include the activated delivery requests, the activated fluid deliveries, completed delivery requests, completed fluid deliveries, and an ordered list of the delivery requests remaining in said second processor service queue.

According to at least one embodiment of the invention, if the communication link 103 between the first processor and the second processor is reestablished, the second processor may enter a recovery synchronization mode while remaining in the active mode, such that the second processor may send status report information to the first processor. The status report information may include one or more of the activated delivery requests, the activated fluid deliveries, completed delivery requests, and completed fluid deliveries. In embodiments that employ a token or semaphore, the PMC may be considered to control the semaphore if the communication link 103, or again 103N for multi-PMC embodiments, is unavailable. In this manner, when the link is reconnected or otherwise restored, the PMC may deliver updated infusion status to the UIC and retain the token.

By way of one or more embodiments of the invention, the user interface application 111 may include indicators, status icons and alarms, as well as one or more buttons such as a power on/off button, a stop button, a silence or mute button, a clean lock button, a load/eject button and any type of information button. In one or more embodiments, the user interface application 111 may include therapy entry and alteration options, such that the therapy entry options may include one or more of basic, concurrent delivery from the two or more channels, bolus, multistep, intermittent infusions and interchannel sequencing therapy delivery. In addition, in one or more embodiments, the alteration options may include one or more of titrating, delay start, piggyback delivery (for example using a second channel then a first channel), bolus and priming options. As such, the system may recover from one or more errors with zero delay in therapy. In at least one embodiment, the alarms may include one or more of a visual alarm and an audio alarm, such that when the communication link between the first processor and said second processor is interrupted, the pump motor controller (PMC) 101 may provide one or more of the visual alarm and the audio alarm on the pump motor controller display. In one or more embodiments, when the communication link 103 between the first processor and the second processor is interrupted, the second processor may display a duration of how long the second processor is able to operate independently of the first processor on the pump motor controller display. In one or more embodiments, the duration may be displayed as a countdown of a time remaining that the second processor is able to operate independently of the first processor on the pump motor controller display.

In one or more embodiments recoverable error conditions such as upstream or downstream occlusions or air related events or motor encoder position error, battery, button, speaker, backlight, drug library download failure, log failure, volume overshoot, temperature or other errors may be displayed by the UIC or PMC for example as alarms in a local or remote manner. Power-on diagnostics for the PMC may test administration sets or cassettes and in case of administration set or cassette error, prompt the user to change administration sets or cassettes and inform the user that the current channel requires service for example. Active run-time diagnostics for the PMC that indicate that the UIC is inoperative and may switch the PMC display information from occlusion pressure, air monitor, etc., related information to an infusion status view that shows information normally displayed on the UIC, albeit in an abbreviated or limited text or graphics based fashion to the extent possible on the limited PMC display. When the UIC recovers or the communication link 103 is available, the PMC will generally then switch back to its normal occlusion, air, etc., display, and update the UIC with current infusion status and continue to execute the therapy program in progress. The UIC will attempt to reboot if a malfunction occurs and request the synchronization data after reboot and power-on diagnostics for example.

Figure 2:
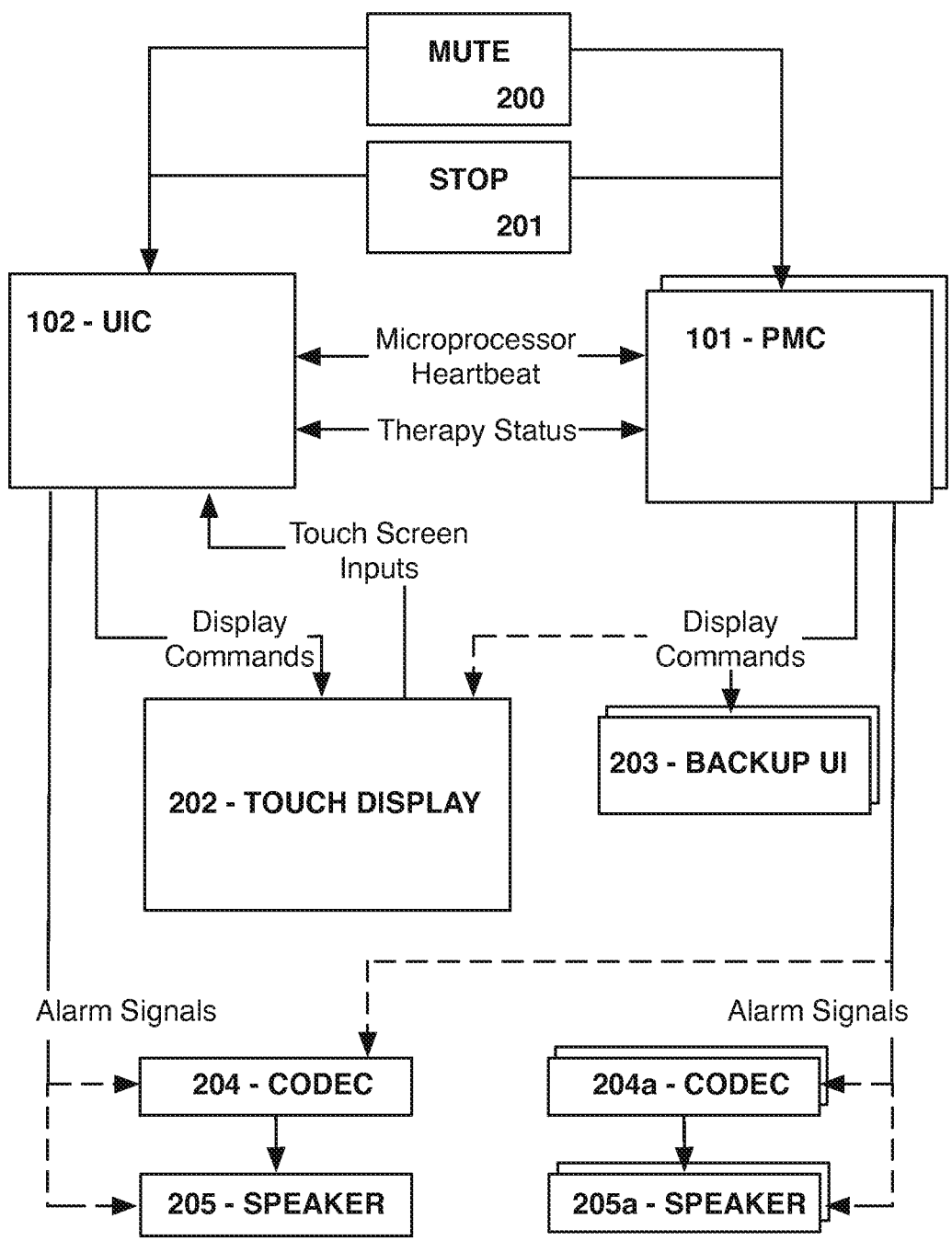
FIG. 2 shows a simplified hardware architectural diagram of the fail-safe drug infusion therapy system according to one or more embodiments of the invention.

FIG. 2 shows an architectural diagram of the fail-safe drug infusion therapy system according to one or more embodiments of the invention. As shown in FIG. 2, the fail-safe drug infusion therapy system may include an emergency stop button 201, a silence or mute button 200, a touch display 202, a backup user interface 203, for example to display infusion related information via the PMC when the UIC is unavailable, a codec 204 and a speaker 205 in communication with the codec 204. More than one PMC may be utilized in the system as depicted by another PMC block shown behind PMC 101. Alternatively, or in combination, the PMC may include multiple backup user interfaces, or they may be associated with respective PMCs. The multiple backup U is are shown as stacked blocks behind backup UI 203. Embodiments may also include multiple codecs and speakers 204a and 205a respectively that are available for use by one or more PMCs. In at least one embodiment of the invention, while the PMC 101 is running and the UIC 102 is unavailable, inoperative or down, the PMC 101 may display rudimentary status messages on backup user interface display 203 or alternatively if a separate communication link exists, on the touch display 202. In one or more embodiments, the optional codec 204 and the speaker 205 may be in direct or indirect communication. The emergency stop button 201 is in communication with the UIC 102 and the PMC 101. As also shown in FIG. 2, the PMC 101 and the UIC 102 may communicate in a bidirectional manner to deliver a microprocessor heartbeat and a therapy status. In at least one embodiment, the UIC 102 may communicate bidirectionally with the touch display 202 in order to deliver display commands from the UIC 102 to the touch display 202, and send touch screen inputs from the touch display 202 to the UIC 102. In one or more embodiments, the PMC 101 may deliver display commands to the backup user interface 203 or optionally to the touch display 202 if an appropriate communication link exists therebetween. In at least one embodiment of the invention, both the PMC 101 and the UIC 102 may delivery alarm signals to the codec 204. In another embodiment of the invention, PMC 101 may delivery alarm signals to a backup speaker 205a or optionally via codec 204a.

By way of one or more embodiments of the invention, if the PMC 101 fails or loses communication with the UIC 102, the UIC 102 may use a redundant set of therapy status information to continue therapy delivery, for example via a different operational PMC channel, wherein the redundant set of therapy status information is updated periodically from the PMC 101. As such, the UIC 102 may hold the current therapy status, wait for the PMC 101 to reboot (if needed) and pass operator (user) intervention. In one or more embodiments, the PMC 101 may perform recovery synchronization and deliver the current status and history log information to the UIC 102, ensuring there is no interruption in therapy history in the log files and automated self-recovery.

Figure 3:
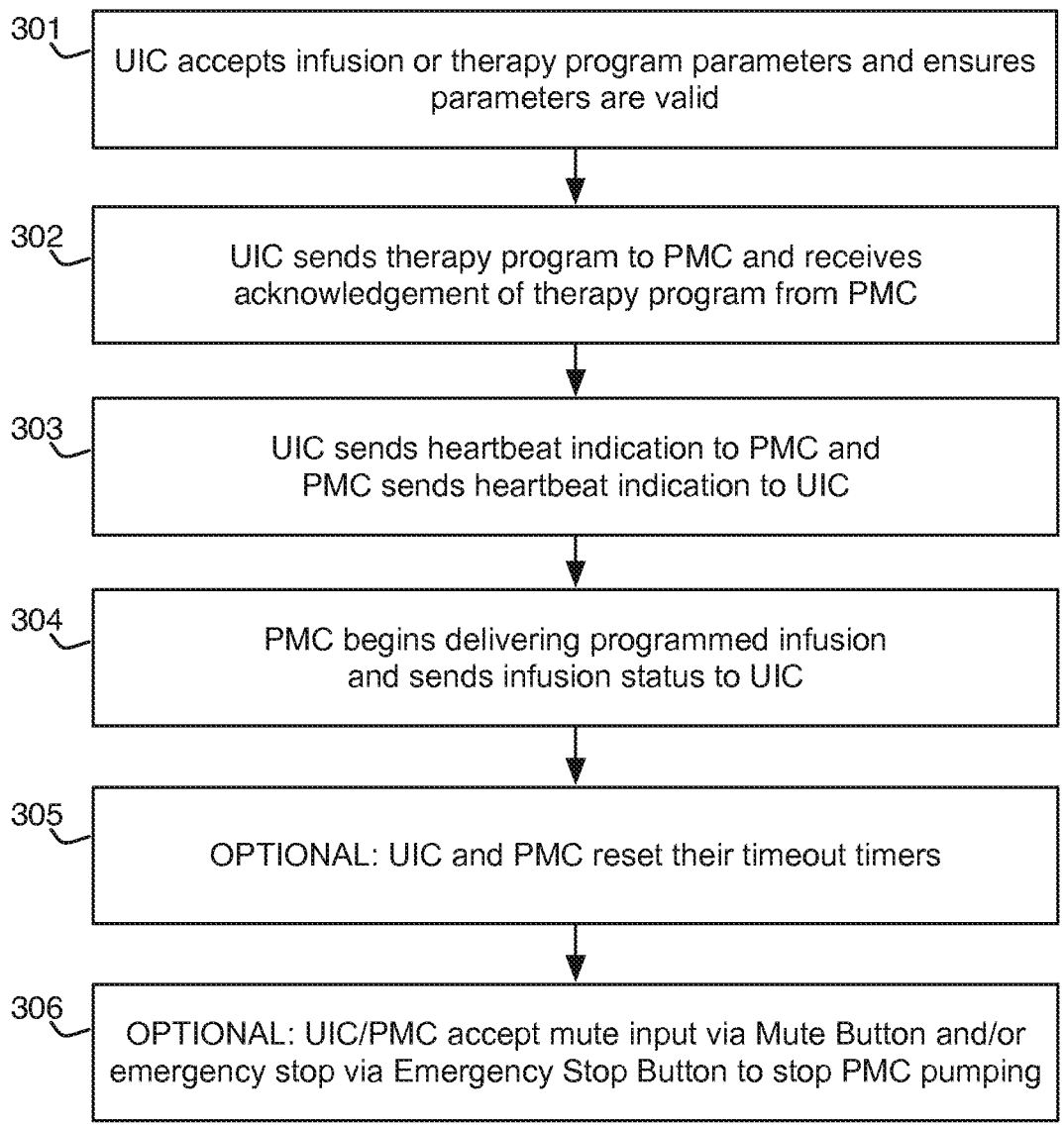
FIG. 3 shows a communications flowchart between the user interface controller and pump motor controller during infusion, according to one or more embodiments of the invention.

FIG. 3 shows a communications flowchart between the user interface controller and pump motor controller during infusion, according to one or more embodiments of the invention. As shown in FIG. 3, under normal operation where both the PMC and UIC are functioning and communicative at 301, the UIC 102 may accept infusion or therapy parameters manually from a user or electronically from another computer system within a hospital (not shown for brevity), and ensure the parameters are valid. In at least one embodiment, at 302 the UIC 102 may send a therapy program to the PMC 101 and receive acknowledgement of the therapy program from the PMC 101. UIC 102 may send a heartbeat indication at 303 to the PMC 101 and a heartbeat indication may be sent from the PMC 101 to the UIC 102. In one or more embodiments, at step 304, the PMC 101 may begin delivering a programmed infusion, or this may occur at any other time after the infusion program is received by the PMC, and the PMC send an infusion status to the UIC 102, wherein the UIC 102 may acknowledge receipt of the infusion status. At step 305, the timeout timers in the UIC and PMC may be optionally reset in software in one or more embodiments, otherwise, timers may be automatically reset if implemented in hardware for example, and the UIC 102 may update status logs. In at least one or more embodiments of the invention, optional step 306 may include accepting a mute input via the Mute Button 200 and/or an emergency stop signal using the emergency stop button 201, for example as accepted by the system from a user, to stop the PMC 101 from pumping. In one or more embodiments, when the emergency stop button 201 is used, the emergency stop signal is simultaneously sent to the UIC 102.

Figure 4:
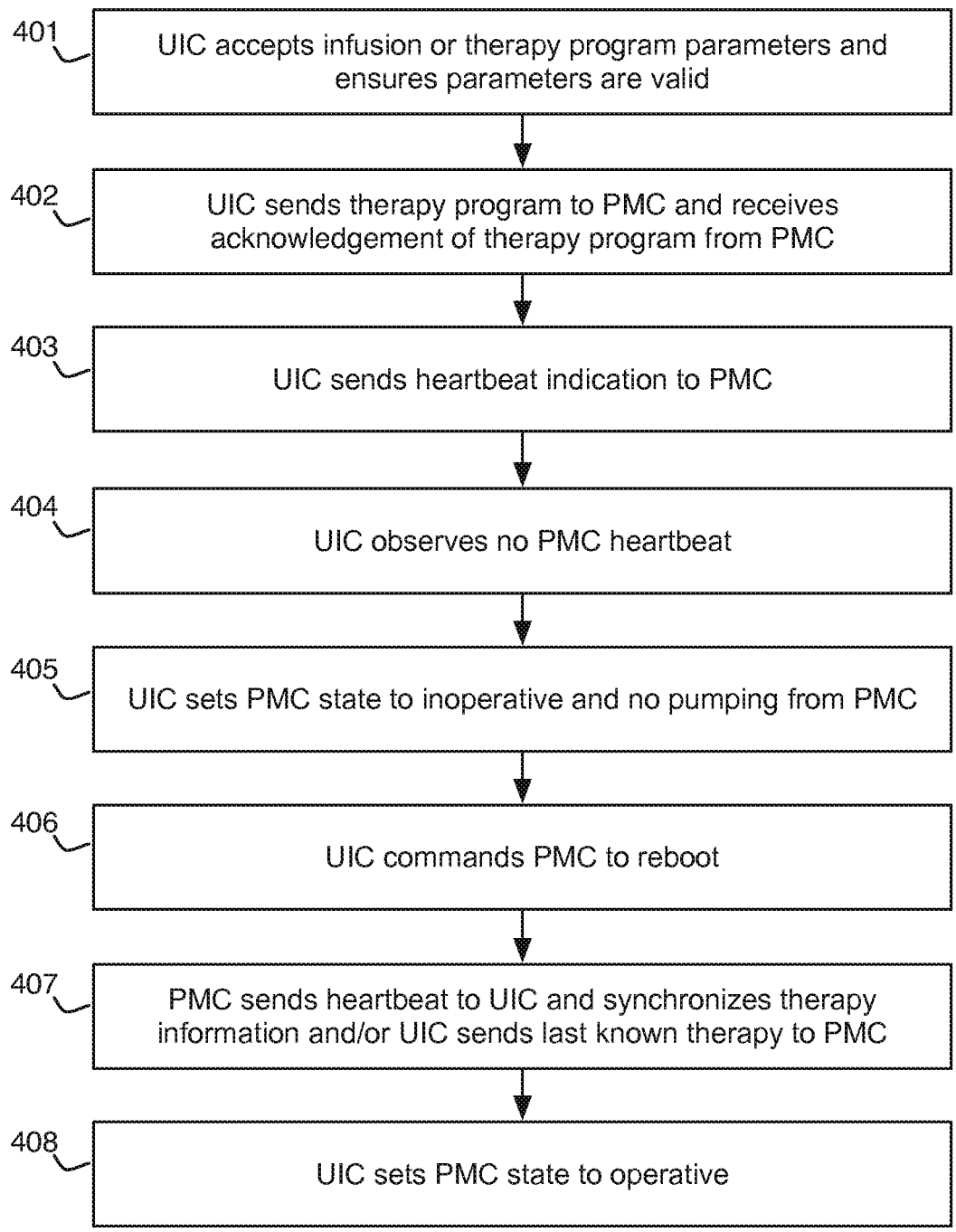
FIG. 4 shows a flowchart illustrating a response to the pump motor controller malfunctioning during infusion, according to one or more embodiments of the invention.

FIG. 4 shows a flowchart illustrating a response due to a pump motor controller malfunction during infusion, according to one or more embodiments of the invention. As shown in FIG. 4, at step 401, the UIC 102 may accept infusion or therapy parameters manually from a user or electronically from another computer system within a hospital (not shown for brevity), and ensure the parameters are valid. In at least one embodiment, at 402 the UIC 102 may send a therapy program to the PMC 101 and receive acknowledgement of the therapy program from the PMC 101. UIC 102 may send a heartbeat indication to the PMC 101 at 403. In one or more embodiments of the invention, the UIC 102 may not receive or otherwise observe a PMC heartbeat at 404, and may then set a PMC state to inoperative at 405, wherein pumping generally does not occur while the PMC 101 is inoperative. At 406, the UIC 102 may command the PMC 101 to reboot, such that the PMC 101 reboots, and at step 407, the PMC 101 then delivers a heartbeat indication to the UIC 102, and the UIC 102 sends a last known therapy to the PMC 101. In one or more embodiments, the PMC 101 may deliver an acknowledgement receipt to the UIC 102 of the last known therapy data, in which at step 408, the UIC 102 may set the PMC state to operative.

Figure 5:
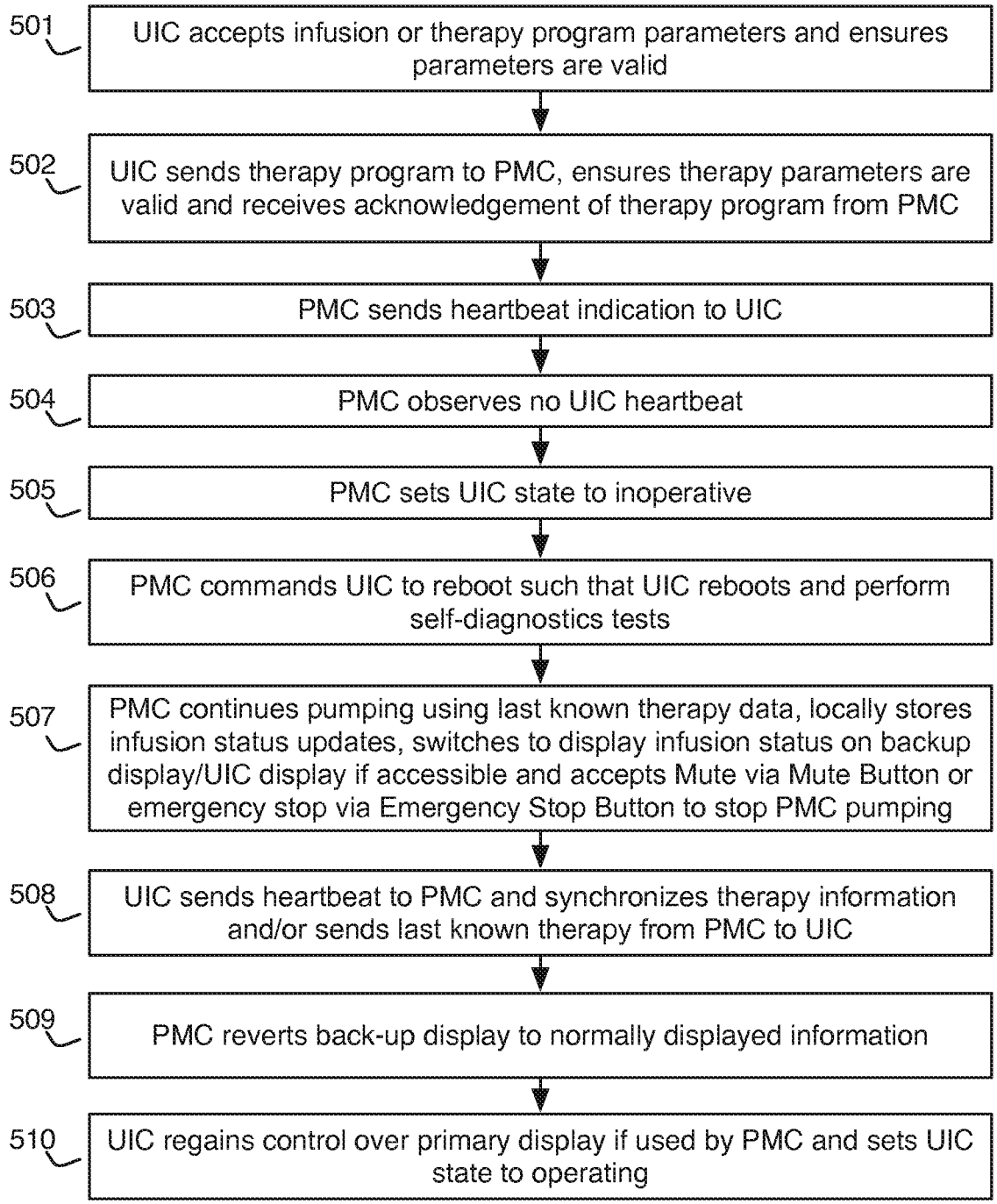
FIG. 5 shows a flowchart illustrating a response to the user interface controller malfunctioning during infusion, according to one or more embodiments of the invention.

FIG. 5 shows a flowchart illustrating a response due to a user interface controller malfunction during infusion, according to one or more embodiments of the invention. As shown in FIG. 5, at step 501, the UIC 102 may accept infusion or therapy parameters manually from a user or electronically from another computer system within a hospital (not shown), and ensure the parameters are valid. In at least one embodiment, at 502 the UIC 102 may send a therapy program to the PMC 101 and receive acknowledgement of the therapy program from the PMC 101. The PMC may send a heartbeat indication to the UIC 102 at 503. In one or more embodiments of the invention, the PMC 101 may not receive or otherwise observe a UIC 102 heartbeat at 504. The PMC may then set a UIC state to inoperative at 505, wherein pumping generally continues while the UIC 102 is inoperative. At 506, the PMC 101 may command the UIC 102 to reboot, or the UIC 102 may auto-reboot wherein in any case the UIC 102 reboots and performs self-diagnostic tests. The self-diagnostic tests may include T0 tests (power-on self-tests), T1 tests (tests prior to therapy start), and T2 tests (infusion active run-time self-diagnostic tests) or any other type of tests. At step 507, the PMC 101 may continue pumping using last known therapy data, locally store infusion status updates, display infusion status for example on backup display 203 or if available on the UIC display 202, as opposed to normal display of information as occurs when the UIC is operational. For example, infusion related status may be displayed albeit on a limited PMC text or graphics based display instead of normal air trap volume, downstream occlusion pressure, or other PMC typical information display. The system may accept a mute input via mute button 200, and/or an emergency stop signal from a user using the emergency stop button 201 in order to stop the PMC 101 from pumping. By way of one or more embodiments, when the emergency stop button 201 is used, the emergency stop signal is simultaneously sent to the UIC 102. In one or more embodiments, when the UIC 102 is inoperative, the touch display 202 may not be available to use a stop option on the touch display 202. In at least one embodiment, at step 508, the UIC 102 may then deliver a heartbeat indication to the PMC 101, and the PMC 101 may send a last known therapy to the UIC 102. In one or more embodiments, the PMC 101 may revert the back-up user interface 203 display to normally displayed information at step 509, and at 510, the UIC 102 may regain control over primary touch display 202 and the PMC 101 may set the UIC state to operating.

In one or more embodiments of the invention, if an error is detected during a T0 test, the system 100 may declare a system malfunction. In one or more embodiments, if an error is detected during a T1 test and the UIC 102 fails, the user may switch infusion channels or communication links or any combination thereof, perform a T1 self-diagnostics test and loop in one embodiment a maximum of three times before declaring a system malfunction. If an error is detected during a T1 test and the PMC 101 declares any malfunction or error, the PMC 101 may attempt to reboot, perform a PMC T0 self-diagnostic test, and if the PMC 101 continues to declare a malfunction or error, then the PMC 101 may declare a system malfunction. In one or more embodiments, optionally, if a dual or multi-channel configuration is used, and the second channel is not in use or inactive, the UIC 102 may move the therapy program to the unused (second) channel and declare that the current (first) channel is inoperative and requires service. During a T1 self-diagnostics test, the UIC 102 cannot declare an error or malfunction since the UIC 102 is not actively involved in therapy.

In one or more embodiments of the invention, if an error is detected during a T2 test and the UIC 102 declares a malfunction or error, each active PMC 101 may activate silence-able backup alarm tone using a mute button, switch backup screen to infusion status view, continue executing the full therapy program, and if the UIC 102 attempts to resynchronize, the PMC 101 may clear backup alarm tone if not muted using mute button, switch backup screen to normal view, such as displaying upstream occlusion pressure, downstream occlusion pressure, upstream air cumulative, downstream air cumulative, upstream air bubble and downstream air bubble, update UIC 102 with current status, such as infusion status and backlog of messages, and the PMC 101 may continue executing the full therapy program. In one or more embodiments of the invention, if an error is detected during a T2 test and the UIC 102 declares a malfunction or error, the UIC 102 may attempt a UIC reboot and perform a T0 self-diagnostics test. In at least one embodiment, if the UIC 102 passes the T0 self-diagnostics test, the UIC 102 may synchronize with the PMC 101, or several PMCs. If the UIC 102 fails the T0 self-diagnostics test, the UIC 102 may declare itself inoperative and state wherein service is required. In one or more embodiments of the invention, if an error is detected during a T2 test and the PMC 101 declares a malfunction or error, the PMC 101 may attempt to reboot itself, perform a T0 self-diagnostics, and if the PMC 101 continues to declare a malfunction or error, then the PMC 101 may declare a system malfunction. In one or more embodiments, optionally, if a dual or multiple channel configuration is used, and the second channel is not in use or inactive, the UIC 102 may move the therapy program to the unused (second) channel and declare that the current (first) channel is inoperative and requires service. In at least one embodiment, if the PMC 101 passes the T0 self-diagnostics test, the UIC 102 may synchronize with the PMC 101 to reprogram the PMC 101 with a current infusion status.

Figure 6:
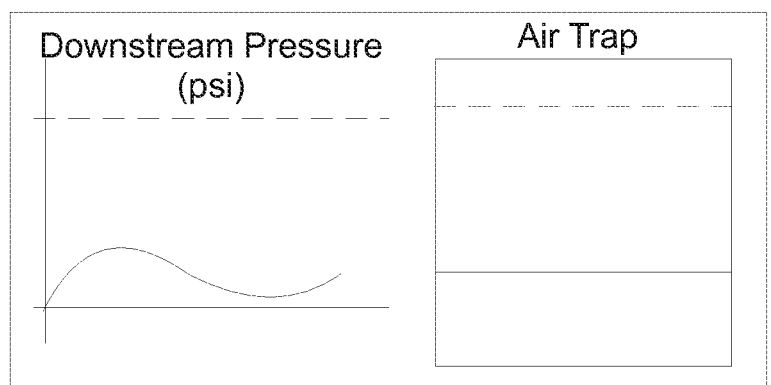
FIG. 6 shows exemplary pump motor controller associated displays under normal operation and under UIC failure wherein the PMC processor, e.g., second processor, is further configured to display a limited version of infusion information on the optional secondary user interface display that is normally displayed by said first processor on the first user interface display.
Figure 6:
Figure 6:

FIG. 6 shows exemplary pump motor controller associated displays under normal operation in the topmost screen. The figure also shows exemplary embodiments of displays under UIC failure wherein the PMC processor, e.g., second processor, is further configured to display a limited version of infusion information on the optional secondary user interface display that is normally displayed by said first processor on the first user interface display. As shown, under normal operation the second user interface display associated with the PMC displays downstream pressure and for example an Air Trap graphical display. Any other information displayed by any PMC is in keeping with the scope of the invention. Under UIC failure as shown in the middle PMC display, the display is switched to a limited version of the UIC display to shown any drugs, infusion programs, and/or other parameters. For example the secondary user interface display may show the battery voltage, e.g., as shown in the right middle screen as a standard battery icon. Any UIC reboot progress may also be displayed. If the UIC fails to reboot, the lower screen may be displayed, which shows the reboot to be unsuccessful and may also display the amount of time that the PMC may operate before infusion ceases.

In addition, one or more embodiments of the invention may include a new drug library parameter, for example a drug library location parameter that enables the UIC and/or PMC to operate in a desired manner associated with the location in which the UIC and PMC are to operate. For example, embodiments may include a new parameter, e.g., "Ward", or "Location-Type" parameters for example, which enables different types of displays, different volume levels for alarms or any other settable parameter for the UIC and/or PMC. This enables General Ward located UIC and PMC's to operate with full volume for alarms while enabling Pediatric Ward located UIC and PMC's to operate with quiet volume alarms so as not to disturb sleeping children. UIC Ward located UIC and PMC's may include other thresholds or alarms for operation that are more sensitive or conservative for example. Any other parameter associated with the UIC and/or PMC may be indexed or otherwise altered by storing an array of parameter values associated with different locations or wards for example. Any other type of data structure that enables UIC and/or PMC settings, for example two or more settings or drug library parameters to be altered by altering the Ward or Location-Type parameter is in keeping with the scope of the invention. In addition, for UIC failure scenarios, this setting enables the PMC to take on the location specific features for alarms in the case of UIC failure, wherein the PMC takes on the responsibility of showing at least a portion of data that the UIC normally shows when operational.

While the invention herein disclosed has been described by means of specific embodiments and applications thereof, numerous modifications and variations could be made thereto by those skilled in the art without departing from the scope of the invention set forth in the claims.

What is claimed is:
1. An infusion pump system comprising:
  a user interface device comprising a display and a first hardware processor; and
  a pump device comprising a motor and a second hardware processor;
  wherein the first hardware processor is configured to:
    transmit infusion parameters to the pump device over a communication link, wherein the second hardware processor is configured to control the motor for delivery of infusion fluid based on the infusion parameters;
    detect a first status of the pump device;
    determine that the pump device is in an inoperative state based on the detected first status;
    command the pump device to reboot; and
    update the pump device after it is rebooted,
    wherein the second hardware processor is configured to determine a time that the second hardware processor is able to operate independently of the first processor and display the time on the display of the user interface device.
2. The infusion pump system of claim 1, wherein the second hardware processor is configured to transmit a status signal at predetermined time periods and wherein the first hardware processor is further configured to detect the first status based on the received status signal from the second hardware processor.

3. The infusion pump system of claim 1, wherein the second hardware processor is further configured to:
  determine that the user interface device is in an inoperative state;
  command the user interface device to reboot;
  continue pumping using last known therapy data;
  store infusion data in a memory of the pump device;
  determine that the user interface device is in an operative state; and
  transmit the infusion data from the memory to the user interface device over the communication link after the determination that the user interface device is in the operative state.

4. The infusion pump system of claim 3, wherein the second hardware processor is configured to control the display of the user interface device based on the determination that the user interface device is in the inoperative state.

5. The infusion pump system of claim 3, wherein the second hardware processor is further configured to process signals received from a mute button.

6. The infusion pump system of claim 1, wherein the first hardware processor is configured to transmit a status signal at predetermined time periods and wherein the second hardware processor is further configured to detect a second status of the user interface device based on the received status signal from the first hardware processor.

7. An infusion pump system comprising:
  a pump device comprising a motor and a first hardware processor, wherein the pump device is configured to receive infusion parameters from a user interface device;
  wherein the first hardware processor is configured to:
    determine that the user interface device is in an inoperative state at a first time;
    command the user interface device to reboot;
    continue pumping infusion fluid using stored infusion parameters;
    determine that that user interface device is in an operative state at a second time after the first time; and
    transmit therapy data acquired between the first time and the second time to the user interface device.

8. The infusion pump system of claim 7, wherein the first hardware processor is further configured to receive a signal from the user interface device, the signal being indicative of an operative state.

9. The infusion pump system of claim 7, wherein the first hardware processor is configured to control a display of the user interface device during the first time and the second time.

10. The infusion pump system of claim 7, wherein the first hardware processor is configured to process a mute signal between the first time and the second time that the user interface device is in the inoperative state.

11. The infusion pump system of claim 7, wherein the first hardware processor is configured to change a display of the pump device to show infusion status during the first time and the second time that the user interface device is in an inoperative state.

12. An infusion pump method for managing a pump device comprising a motor and a first hardware processor, wherein the pump device is configured to receive infusion parameters from a user interface device, the infusion pump method comprising:
  determining, by the first hardware processor, that the user interface device is in an inoperative state at a first time;
  commanding, by the first hardware processor, the user interface device to reboot;
  continuing, by the first hardware processor, pumping infusion fluid using stored infusion parameters;
  determining, by the first hardware processor, that user interface devices is in an operative state at a second time after the first time; and
  transmitting, by the first hardware processor, therapy data acquired between the first time and the second time to the user interface device.

13. The infusion pump method of claim 12, further comprising receiving a signal from the user interface device, the signal being indicative of operative state.

14. The infusion pump method of claim 12, further comprising controlling a display of the user interface device during the first time and the second time.

15. The infusion pump method of claim 12, further comprising processing a mute signal between the first time and the second time that the user interface device is in an inoperative state.

16. The infusion pump method of claim 12, further comprising changing a display of the pump device to show infusion status during the first time and the second time that the user interface device is in an inoperative state.

* * * * *